(12) United States Patent
Garza et al.

(10) Patent No.: US 11,452,497 B2
(45) Date of Patent: Sep. 27, 2022

(54) INJECTABLE HEMODYNAMIC MONITORING DEVICES, SYSTEMS AND METHODS

(71) Applicant: CoraVie Medical, Inc., Edina, MN (US)

(72) Inventors: Aimee Garza, Edina, MN (US); Tanzania Sewell, Kalamazoo, MI (US)

(73) Assignee: Coravie Medical, Inc., Edina, MN (US)

( * ) Notice: Subject to any disclaimer, the term of this patent is extended or adjusted under 35 U.S.C. 154(b) by 0 days.

(21) Appl. No.: 17/493,500

(22) Filed: Oct. 4, 2021

(65) Prior Publication Data
US 2022/0022844 A1   Jan. 27, 2022

Related U.S. Application Data

(63) Continuation of application No. PCT/US2021/033138, filed on May 19, 2021.

(60) Provisional application No. 63/026,878, filed on May 19, 2020.

(51) Int. Cl.
*A61B 8/12* (2006.01)
*A61B 8/02* (2006.01)
*A61B 8/04* (2006.01)
*A61B 8/08* (2006.01)
(Continued)

(52) U.S. Cl.
CPC .................. *A61B 8/12* (2013.01); *A61B 8/02* (2013.01); *A61B 8/04* (2013.01); *A61B 8/5207* (2013.01); *A61B 8/5276* (2013.01); *A61B 8/565* (2013.01); *A61B 17/3468* (2013.01);
(Continued)

(58) Field of Classification Search
CPC ........ A61B 8/04; A61B 8/02; A61B 2562/028
See application file for complete search history.

(56) References Cited

U.S. PATENT DOCUMENTS 5,113,869 A * 5/1992 Nappholz ............ A61B 5/0006
128/903
5,207,644 A * 5/1993 Strecker ............ A61M 39/0208
604/164.01
(Continued)

FOREIGN PATENT DOCUMENTS

| WO | 2006122750 A1 | 11/2006 |
| WO | 2018220143 A1 | 12/2018 |
| WO | 2020131727 A1 | 6/2020 |

OTHER PUBLICATIONS

Ma, Yinji et al., Relation Between Blood Pressure and Pulse Wave Velocity for Human Arteries; PNAS, Oct. 30, 2018, vol. 115, No. 44, 11144-11149; www.pnas.org/cgi/doi/10.1073/pnas.1814392115.
(Continued)

*Primary Examiner* — Oommen Jacob
(74) *Attorney, Agent, or Firm* — Downs Rachlin Martin PLLC

(57) ABSTRACT

An implantable sensor system using one or more sensor implants comprised of micro-electrical mechanical system (MEMS) sensors for the accurate and continuous measurement of physiological hemodynamic signals such as diastolic and systolic blood pressure. Sensor implants are configured to be subcutaneously injected to a placement site adjacent a blood vessel. In some embodiments, sensors comprise micromachined ultrasonic transducers.

23 Claims, 11 Drawing Sheets

(51) Int. Cl.
*A61B 8/00* (2006.01)
*A61B 17/34* (2006.01)

(52) U.S. Cl.
CPC . *A61B 2562/028* (2013.01); *A61B 2562/0219* (2013.01); *A61B 2562/0271* (2013.01)

(56) References Cited

U.S. PATENT DOCUMENTS

| | | | |
|---|---|---|---|
| 5,309,916 A * | 5/1994 | Hatschek | A61B 5/0285 600/452 |
| 5,564,434 A | 10/1996 | Halperin et al. | |
| 6,024,704 A * | 2/2000 | Meador | A61B 5/0215 128/899 |
| 6,053,873 A | 4/2000 | Govari et al. | |
| 6,077,227 A | 6/2000 | Miesel et al. | |
| 6,106,477 A | 8/2000 | Miesel et al. | |
| 6,354,999 B1 * | 3/2002 | Dgany | A61B 1/015 600/561 |
| 6,398,734 B1 * | 6/2002 | Cimochowski | A61B 5/6884 600/459 |
| 6,409,674 B1 | 6/2002 | Brockway et al. | |
| 6,468,219 B1 * | 10/2002 | Njemanze | A61B 8/065 607/23 |
| 7,035,684 B2 | 4/2006 | Lee | |
| 7,416,530 B2 | 8/2008 | Turner et al. | |
| 7,483,743 B2 | 1/2009 | Mann et al. | |
| 7,682,313 B2 | 3/2010 | Bodecker et al. | |
| 7,686,762 B1 | 3/2010 | Najaf et al. | |
| 7,996,092 B2 | 8/2011 | Mrva et al. | |
| 8,127,618 B1 | 3/2012 | Zhao et al. | |
| 8,231,538 B2 | 7/2012 | Aebersold et al. | |
| 8,457,746 B2 | 6/2013 | Libbus | |
| 8,521,282 B2 * | 8/2013 | Czygan | A61N 1/36528 600/468 |
| 8,548,592 B2 | 10/2013 | Mi et al. | |
| 8,573,062 B2 | 11/2013 | Zhao et al. | |
| 8,602,999 B2 | 12/2013 | Young et al. | |
| 8,750,983 B2 * | 6/2014 | Bonutti | A61B 8/00 604/20 |
| 9,089,691 B2 | 7/2015 | Libbus et al. | |
| 9,220,906 B2 | 12/2015 | Griswold et al. | |
| 9,227,053 B2 | 1/2016 | Bonde et al. | |
| 9,498,130 B2 | 11/2016 | Najaf et al. | |
| 9,681,843 B2 | 6/2017 | Baru et al. | |
| 10,173,069 B2 | 1/2019 | Taepke et al. | |
| 10,314,501 B2 | 6/2019 | Zitnik et al. | |
| 10,820,888 B2 | 11/2020 | Boser et al. | |
| 10,864,553 B2 | 12/2020 | Sammoura et al. | |
| 11,253,159 B2 * | 2/2022 | Shusterman | A61B 5/02007 |
| 2005/0131468 A1 * | 6/2005 | Echt | A61H 31/006 607/9 |
| 2005/0154299 A1 * | 7/2005 | Hoctor | A61B 8/4236 600/437 |
| 2005/0200241 A1 * | 9/2005 | Degertekin | B06B 1/0292 310/334 |
| 2006/0211942 A1 * | 9/2006 | Hoctor | A61B 5/02125 600/485 |
| 2008/0021325 A1 * | 1/2008 | Drost | A61B 8/4227 600/454 |
| 2008/0091255 A1 | 4/2008 | Caparso et al. | |
| 2008/0177366 A1 | 7/2008 | Bolea et al. | |
| 2009/0157058 A1 * | 6/2009 | Ferren | A61B 5/6807 604/891.1 |
| 2010/0217136 A1 | 8/2010 | Turner et al. | |
| 2010/0274321 A1 | 10/2010 | Libbus | |
| 2010/0298720 A1 | 11/2010 | Potkay et al. | |
| 2011/0009754 A1 | 1/2011 | Wenzel et al. | |
| 2012/0209088 A1 | 8/2012 | Romem | |
| 2012/0215117 A1 * | 8/2012 | Karst | A61N 1/36585 600/486 |
| 2013/0178750 A1 | 7/2013 | Sheehan et al. | |
| 2014/0135815 A1 * | 5/2014 | Hyde | A61B 8/0891 606/200 |
| 2018/0177486 A1 | 6/2018 | Gifford et al. | |
| 2019/0076033 A1 | 3/2019 | Sweeney et al. | |
| 2019/0184113 A1 * | 6/2019 | Sienko | A61M 5/42 |
| 2020/0253583 A1 * | 8/2020 | Brisken | A61B 8/0891 |
| 2022/0022844 A1 * | 1/2022 | Garza | A61B 8/5223 |

OTHER PUBLICATIONS

Wang, Chonghe et al., Monitoring of the Central Blood Pressure Waveform via a Conformal Ultrasonic Device; Nature Biomedical Engineering; Articles; vol. 2, Sep. 2018, pp. 687-695; www.nature.com/natbiomedeng.

Shelton, Stefon et al., Aluminum Nitride Piezoelectric Micromachined Ultrasound Transducer Arrays; Solid-State Sensors, Actuators, and Microsystems Workshop; Hilton Head Island, South Carolina, Jun. 3-7, 2012; 9780964002494/HH2012; pp. 291-294.

International Search Report and Written Opinion dated Aug. 30, 2021, in connection with PCT/US2021/033138, filed May 19, 2021.

* cited by examiner

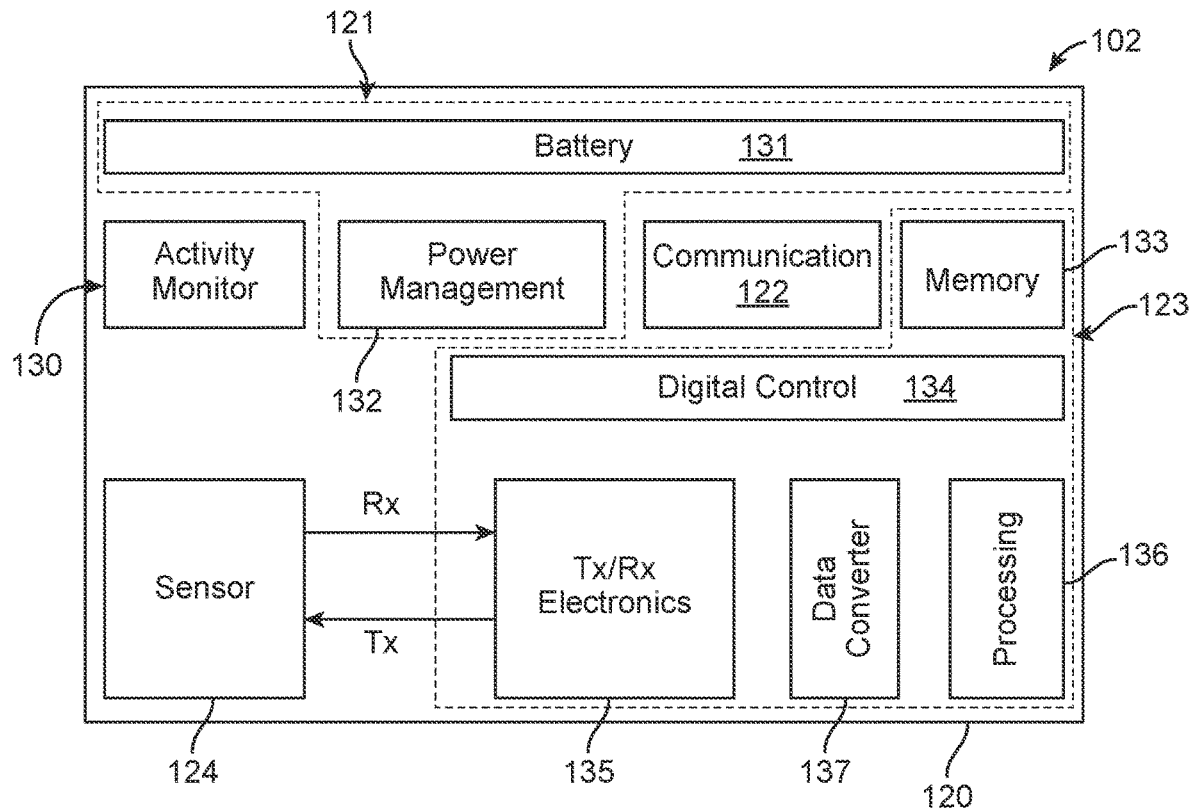
FIG. 3
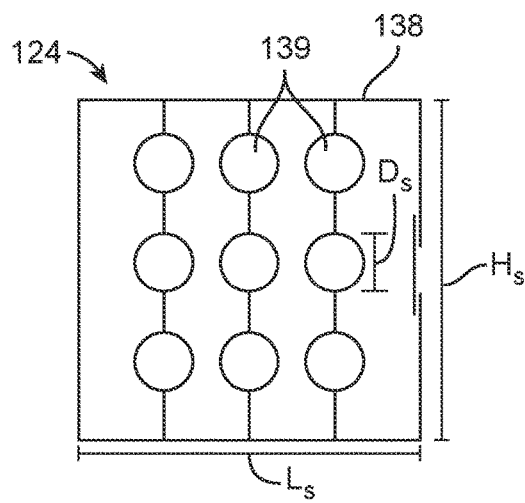
FIG. 3A
FIG. 3B

INJECTABLE HEMODYNAMIC MONITORING DEVICES, SYSTEMS AND METHODS

RELATED APPLICATIONS

This application is a continuation of PCT Application No. PCT/US21/33138, filed on May 19, 2021, and titled "Injectable Hemodynamic Monitoring Devices, Systems and Methods"; which international application claims priority to U.S. Provisional Application No. 63/026,878, filed May 19, 2020, entitled "Injectable Blood Pressure Monitoring Systems and Methods". Each of these applications is incorporated herein in its entirety.

FIELD

The present disclosure generally relates to the field of miniaturized implantable vital signs monitoring devices and methods. In particular, the present disclosure is directed to subcutaneously injectable blood pressure monitoring systems and methods suitable, inter alia, for long-term monitoring of cardiovascular signals.

BACKGROUND

Hypertension is a significant precursor to cardiovascular disease and death. It is estimated that there are 1.6 billion people worldwide with hypertension, over 100 million in the United States alone, and less than one-third are under control. Hypertension is costly and deadly. There are an estimated 7.8 million deaths each year due to hypertension, and it costs the United States an estimated $131 billion annually due to lost productivity and healthcare costs. Due to its deadliness and costs, it has been a target of government, academic, for-profit, and non-profit organizations. A recent task force has been formed to help reduce the incidence and prevalence of hypertension.

While there are many effective therapies and management protocols to prevent the progression of cardiovascular disease, patients and clinicians are challenged to achieve optimal management for a variety of reasons. First, hypertension is largely asymptomatic. Patients are often unaware they have hypertension which creates skepticism and doubt whether they need to take their prescribed medications or follow diet and exercise recommendations. Secondly, doctors only have sporadic, point-in-time data with varying accuracy of the measurement taken when it is taken outside the clinic. When measurements are taken in a clinic setting, patients may experience either White Coat Syndrome, or Masked Hypertension. This lack of consistent and accurate blood pressure data and trends decreases confidence in the right medical management decisions. Clinicians do not have enough data to make an accurate therapeutic change that could benefit the patient.

Current practices to improve blood control status and management include home blood pressure monitoring and ambulatory blood pressure monitoring. Many patients use, and clinicians prescribe, home blood pressure monitors to augment in-clinic measurements. These traditional home blood pressure monitors are point-in-time and require the patient to take action regularly, and to have cognitive physical ability to accurately place the blood pressure cuff and collect multiple measurements that can be averaged to filter out inaccuracies or outliers. Another challenge with traditional home blood pressure monitoring is that it does not allow a patient to take their blood pressure at night for obvious reasons. It is also not possible to capture blood pressure readings during different activities compared to resting. Clinical research has demonstrated the clinical relevance and importance of day vs. night blood pressure and the relationship to when medications are administered.

Another prescribed technology is Ambulatory Blood Pressure Monitoring (ABPM). Recent FDA approvals and CMS coverage decisions for ABPM are promising and the technology addresses some of the challenges of traditional home blood pressure monitoring systems. But the technology continues to be a barrier to patient and physician adoption. ABPM technology available today uses traditional sphygmomanometer methods to capture blood pressure measurements every 15 minutes for a period of 24-48 or even 72 hours. While the patient can be "ambulatory", the patient wears a cuff that inflates as often as every 15 minutes continuously for up to 72 hours causing pain and bruises. It keeps the patient awake at night, and it is an inconvenient system to wear during activities or even during a working day. It is intrusive into the patient's life and indiscreet.

Accordingly, there remains a clinical need for effective and minimally invasive and minimally intrusive methods to monitor and track blood pressure continuously over time.

SUMMARY

In one implementation, the present disclosure is directed to a hemodynamic monitoring method, which includes subcutaneously placing a sensor implant in a patient in tissue adjacent a target blood vessel; generating a data stream with the sensor implant from which pulse wave velocity of the target blood vessel during a sensing period can be determined; and transmitting the data stream to a computing device configured to determine pulse wave velocity for the target blood vessel and blood pressure for the patient using the data stream.

In another implementation, the present disclosure is directed to a hemodynamic monitoring method including patient blood pressure monitoring using a subcutaneously placed sensor implant having first and second ultrasound sensors spaced apart at fixed distance. The method includes receiving an ultrasound imaging signal from the first ultrasound sensor depicting imaging of a target blood vessel at a first sensing location; detecting a cardiac cycle pulse in the first imaging signal; receiving an ultrasound imaging signal from the second ultrasound sensor depicting imaging of the target blood vessel at a second sensing location spaced at a sensing distance from the first sensing location; detecting the cardiac cycle pulse in the second imaging signal; determining the sensing distance based on the fixed distance and the first and second imaging signals; measuring time between the detection of the cardiac cycle pulse at the first and second sensing locations; detecting patient movement during a timeframe encompassing the detecting of the cardiac cycle pulse at the first and second sensing locations; and transmitting a signal containing data representing the detected patient movement, determined sensing distance and measured time for receipt at a computing device outside a patient's body configured to determine patient blood pressure during the timeframe based on the data contained in the transmitted signal.

In yet another implementation, the present disclosure is directed to a hemodynamic monitoring method, which includes (a) subcutaneously placing a sensor implant in a patient in tissue at a placement location outside a target blood vessel within about 2 mm to about 50 mm of the target blood vessel, the implant comprising at least one sensor configured to detect changes in vessel diameter at first and second spaced apart sensing locations along the vessel, wherein a distance between the first and second sensing locations along the vessel varies based on orientation of the implant with respect to the vessel; (b) with the sensor implant—detecting vessel diameter at the first and second sensing locations; and generating a data stream correlated to a sensing period, the data stream comprising—data representative of a change in target vessel diameter at the first sensing location, data representative of a change in target vessel diameter at the second sensing location, data representative of the distance between the first and second sensing locations, data representative of a time difference between the change in target blood vessel diameter at the first sensing location and the second sensing location, data representative of patient movement or change in position, and data representative of vessel inner and outer diameter; and (c) transmitting the data stream to an external system, whereby the data stream is accessible by a computing device to determine pulse wave velocity for the vessel and patient blood pressure during the sensing period based on the data stream.

In still another implementation, the present disclosure is directed to a hemodynamic sensor system, which includes a sensor implant, comprising a housing configured and dimensioned to be delivered subcutaneously through a hollow introducer sheath into tissue adjacent a target blood vessel in a patient, and at least one tissue fixation feature on an outer surface of the housing, the sensor implant further comprising within the housing; at least one sensor module configured to detect changes in one or more physiological parameters indicative of patient hemodynamic condition, wherein at least one the sensor module comprises an ultrasound transducer; and a communication module communicating with the at least one sensor module to transmit one or more signals comprising signals representative of the detected changes to an external receiver.

BRIEF DESCRIPTION OF DRAWINGS

For the purpose of illustrating the disclosure, the drawings show aspects of one or more embodiments of the disclosure. However, it should be understood that the present disclosure is not limited to the precise arrangements and instrumentalities shown in the drawings, wherein:

FIG. 3 is a block diagram illustrating principle functional components in embodiments of sensor implants disclosed herein.

FIG. 3A is sensor state diagram for an embodiment of a sensor module of the present disclosure.

FIG. 3B is schematic illustration of a sensor element array for a pMUT or cMUT sensor module as disclosed herein.

DETAILED DESCRIPTION

Figure 1:
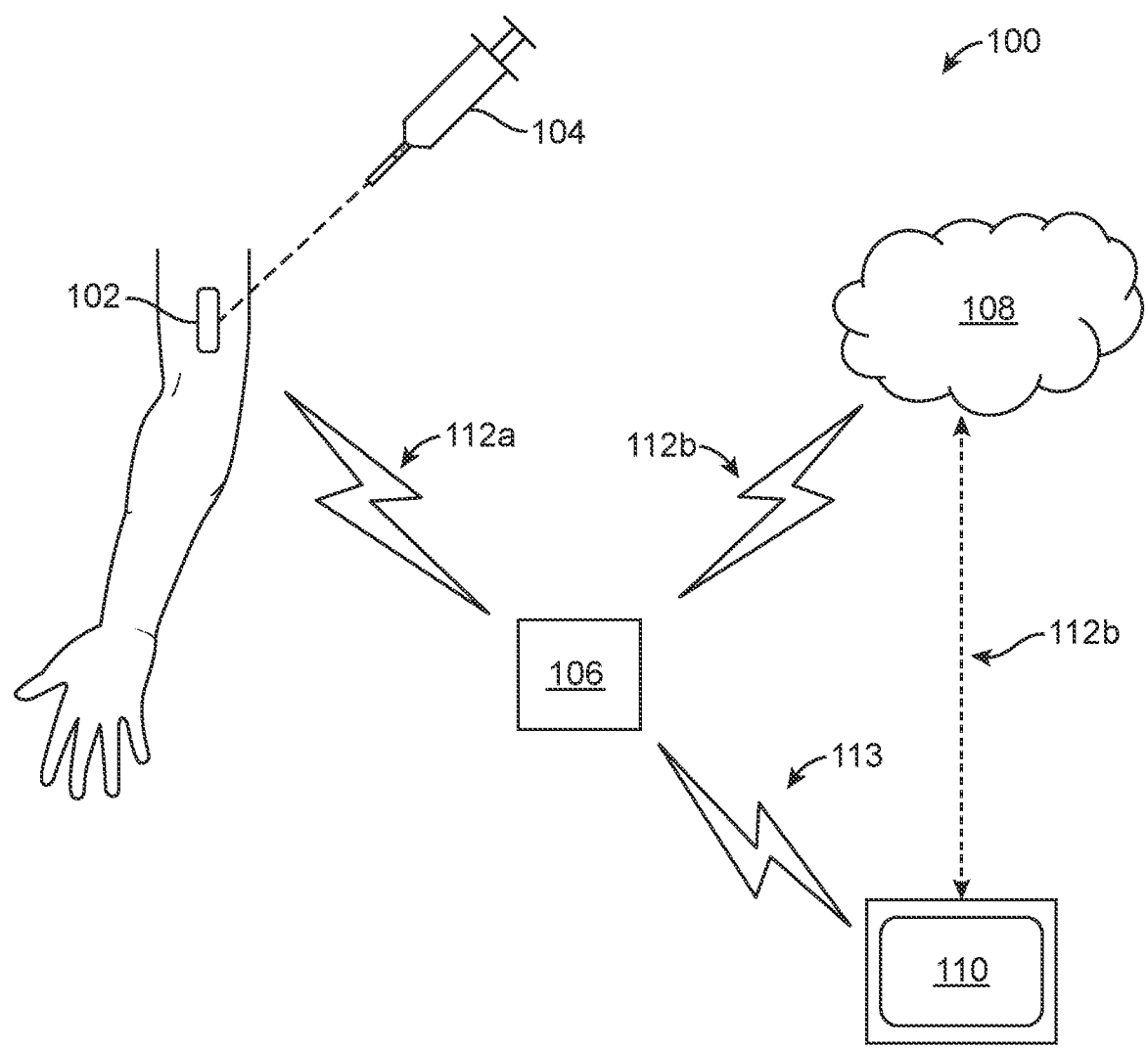
FIG. 1 is a schematic depiction of an overall system according to an embodiment of the present disclosure.

Embodiments of the present disclosure provide unobtrusive, minimally invasive, active implantable sensor devices, sensor systems and methods that meet current clinical needs. Disclosed devices, systems and methods use one or more micro-electrical mechanical system (MEMS) sensors for the accurate and continuous measurement of physiological hemodynamic signals such as diastolic and systolic blood pressure. In certain variations, embodiments disclosed herein may include any, or all, of the following additional clinical signals of overall patient status: heart rate, activity level (patient movement or position), temperature, heart rate variability, and stenosis. Disclosed embodiments can provide a long-term sensor system will provide accurate (equivalent to current standard of care) blood pressure over an extended duration (for instance, months or years), enabling the clinician to provide appropriate treatment recommendations.

The use of microelectromechanical systems (MEMS) manufacturing techniques in disclosed embodiments provides a unique micro-sized design, construction, and fixation that allows the implanted sensor system to be fixated just outside the target blood vessel wall, or in some alternatives in the vessel wall, using methods familiar to clinicians trained in accessing a blood vessel (such as ultrasound-guided imaging, and standard needle and syringe access to artery) and minimally invasive outpatient procedures. MEMS construction, unique materials and resultant miniaturized design also promotes efficient use of power compared to more conventional ultrasound transducers. Typical sizes of disclosed sensor implants are millimeter size scale; for example, in some embodiments sensor implant size will have dimensions ranging from about 1 mm to about 30 mm in any of length, width and height directions, and more typically may be in the range 2.5-7.5 mm width×15-30 mm length×2-4 mm height. Novel injection tools enable the sensor implant to be inserted in an outpatient or clinic setting within minutes. A benefit of a clinic setting is that the patient acceptance increases, and more physicians will be skilled/trained in the minimally invasive procedure.

Persons skilled in the art will appreciate various features and advantages of devices, systems and methods of the present disclosure, including, but not limited to active implant (battery or inductively powered) to help reduce patient compliance challenges; fixation mechanism that allows the sensor system to be injected, but fixated outside the artery (in some embodiments, e.g. extravascular) to help reduce thrombus that can lead to signal drift and decreased sensitivity, minimize dislodgement, and clot adverse events compared to an intravascular sensor; MEMS-based-sensor module that incorporates one or more of sensors (strain/piezoelectric resistive transducer, piezoelectric/capacitive ultrasound); biocompatible nano-coatings to minimize encapsulation/biofouling; and ability to continuously capture and store cardiovascular signals for an extended duration.

As illustrated in FIG. 1, components of a basic system 100 according to the present disclosure may comprise injectable sensor implant 102, injection device 104, local control module 106, network-based analytics and data management modules 108 and clinician module 110 comprising user interfaces/applications for data access, analysis and alerts. Local control module 106 may take a variety of forms. In some embodiments, module 106 may comprise simply a communications module, facilitating communication between sensor implant 102 and network-based modules 108 and/or clinician module 110. In other embodiments, in addition to a communications sub-module, local module 106 may include processing and/or data storage sub-modules configured to store patient data from sensor implant 102 and/or determine patient parameters, such as blood pressure and fluid status, as described herein below. Module 106 also may function as an edge device for communication with network-based analytics, storage and data management modules. Module 106 thus may comprise one or more processors, memories and associated computing components commensurate with the functionality of module 106 in a specific configuration as may be devised by persons skilled in the art based on the teachings of the present disclosure. In some embodiments, local control module 106 may comprise a personal mobile device, such as a cell phone or tablet, running a downloadable app.

Clinician module 110 may comprise wirelessly connected devices such as computers, cell phones or tablets. Clinician module 110 also may be configured as a patient interface. In some embodiments, particularly where configured as a patient interface, module 110 may comprise an app running on the same device as running an app for local module 106. In some embodiments, the functionality of both modules 106 and 110 may be incorporated into a single app executed on a mobile device.

Wireless communication links 112a and 112b are provided between sensor implant 102, local module 106 and network-based analytics or data management modules 108. Communication link 112b also may comprise a wired communication link. Communication links 113 between local module 106 and user interfaces 110 may be wired or wireless. Additionally, clinician module 110 may communicate directly with network-based analytics module 108. Communication links 112a, 112b and 113 may comprise any of a number of known communication protocols. For example, communication link 112a may comprise a personal area network (PAN) using communications based on technologies such as IrDA, Wireless USB, Bluetooth or ZigBee. Communication links 112b, 113 may comprise longer range, larger bandwidth communications such as LAN, WLAN or IAN. In a further alternative embodiment, one or more sensor implants 102 may communicate wirelessly with other sensor types of sensor modules via a body area network (BAN).

Figure 2:
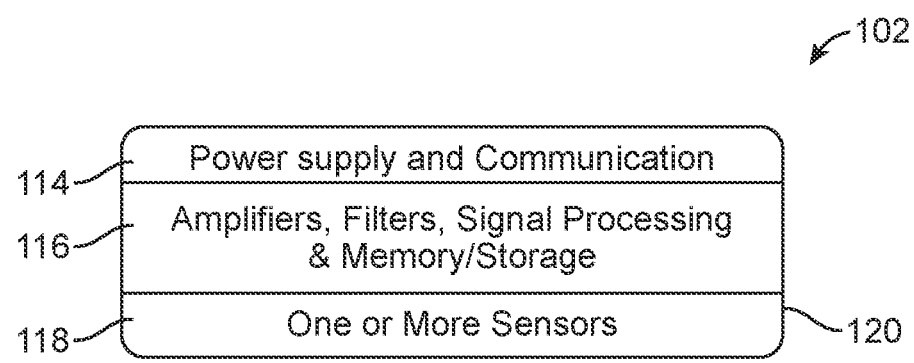
FIG. 2 is block diagram illustrating functional modules of sensors as disclosed herein.

As shown in FIG. 2, sensor implants 102 according to the present disclosure may generally comprise a layered MEMS structure with typically three functional layers made up of functional modules and sub-modules: power supply and communication layer 114 comprising elements such as a primary cell batteries conventionally used to power micro-sized medical implants or, in some embodiments, a solid state lithium ion rechargeable battery and RF antenna for charging and communication, ASIC and memory layer 116 comprising amplifiers, filters, processing and memory storage, and sensor layer 118 comprising one or more sensor modules, which may comprise piezoelectric micromachined ultrasonic transducers (pMUT) or capacitive micromachined ultrasonic transducers (cMUT). In some embodiments, capacitive pressure sensing may be employed. Other sensing modules may be configured as patient status sensors with additional sensing capabilities as described herein below. Functional layers 114, 116 and 118, together comprise a sensor package contained within a biocompatible housing 120. In some embodiments, power supply and communication layer 114 may be configured for inductive coupling for charging and/or communications.

Figure 2A:
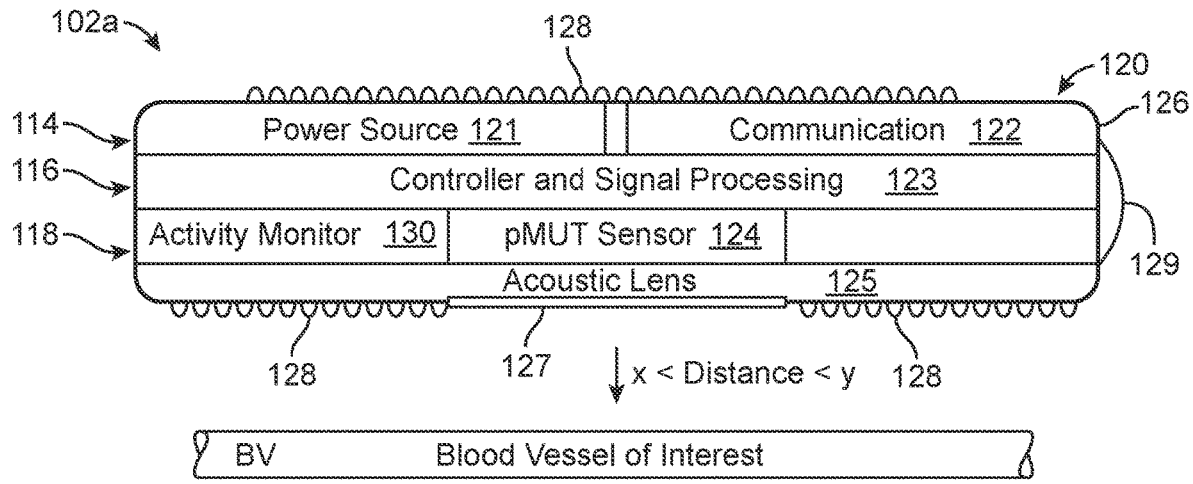
FIGS. 2A, 2B and 2C are block diagrams illustrating in more detail functional modules of alternative embodiments of sensors.
Figure 2B:
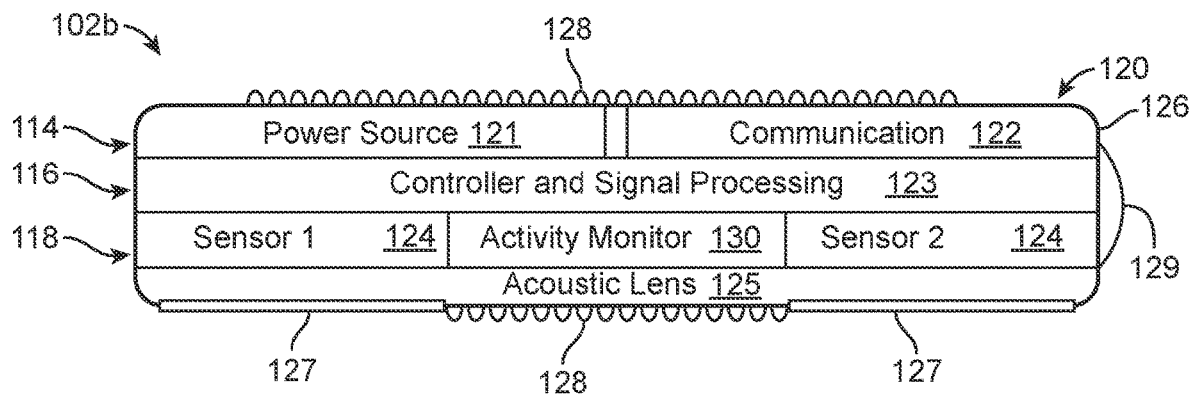
Figure 2C:
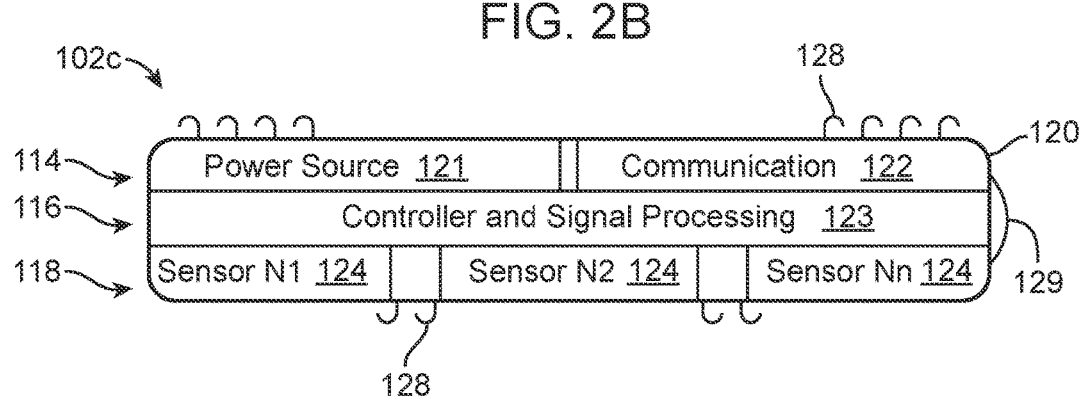

The layered MEMS structures described herein provide actively powered, integrated sensor implants well-suited to long-term sub-cutaneous and extravascular monitoring of blood pressure and other cardiovascular vital signs using ultrasound (US). The disclosed structures thus address challenges of previous approaches to collect reliable continuous blood pressure over time. FIGS. 2A, 2B and 2C illustrate a number of alternative configurations for sensor implant 102 that achieve these advantages.

Sensor implant 102a, shown in FIG. 2A, includes power module 121 and communications module 122 in functional layer 114. In some embodiments where inductive power coupling is used as the power source, the power module 121 and communications module 122 may be integrated as a single communications/power source module. Control and signal processing module 123 resides in functional layer 116. In this embodiment, MUT sensor array 124, along with status sensor module 130 and optional acoustic lens 125 comprise sensor layer 118. This layered MEMS structure is contained within biocompatible housing 120. In some embodiments, housing 120 may comprise rigid materials such as titanium, stainless steel or nitinol. Biocompatible plastics or silicone also may be used as a housing material. If the material for housing 120 is not freely transmissive of US signals, one or more appropriate US transmissive window(s) 127 may be provided aligned with US sensor array 124, such that housing 120 may comprise non-US transmissive portions 126 and transmissive portions 127. Materials for US transmissive window(s) 127 include biocompatible materials such as polydimethylsiloxane (PDMS), silicone, glass, ceramic or parylene coatings.

Outer surfaces of housing 126 may be provided with a coating of materials to promote tissue adhesion, such as collagen, fibrin, chitosan, hyaluronic acid, and alginate, and/or may have textured, roughened or featured surfaces for this purpose. Other surfaces, such as US transmissive windows 127, may have coatings to prevent tissue adhesion. Examples of adhesion preventative coatings include polymer brushes and self-assembled monolayers. As shown in FIG. 2A, fixation features 128 may comprise three-dimensional surface irregularities designed to create friction and prevent device migration over time. These irregularities may be rigid structures or compliant structures, such as fabric mesh or loops. In other embodiments, retractable tines with memory and flexibility (nitinol) are optimally placed to promote stable implant position over time. Fixation tines are collapsible and are collapsed inside of an insertion tool and engage when released from the insertion tool. Alternatively, one or more wings, or flaps, are optimally placed to promote stable implant position over time, and may be configured to collapse when inside the insertion tool and engage when released from the insertion tool. In some embodiments, fixation features 128 also may be configured as antennas as a part of communications module 122. Sensor implants 102 also may include an attachment and release feature 129 on an outer surface of housing 126. Attachment and release feature 129 may comprise a loop or recess that is releasably engageable by a delivery and retrieval mechanism as described in more detail below.

As indicated in FIG. 2A, extravascular sensor implants according to the present disclosure are preferably positioned at a known distance from the outer wall of the blood vessel (BV) to be interrogated. Optimum placement distance from the blood vessel may be set by persons of ordinary skill based on the teachings of the present disclosure taking into account parameters such as a sensor array configuration, tuning of the US signal using system electronics and selection of an acoustic lens. An advantage of injection devices 104 hereinafter described is that they allow for precise placement at a preferred sensing distance using visualization such as external ultrasound visualization. In some embodiments, sensing distance from the blood vessel outer wall will be in the range of about 2 mm to about 50 mm. In other embodiments, a narrower distance range of about 3 mm to about 15 mm may be preferable and, in some cases, a placement of 5 mm to 7 mm may be ideal.

While sensor implant 102a includes only a single sensor array 124, often it will be preferable to include at least two, spaced-apart sensor arrays 124 in order to facilitate pulse wave velocity (PWV) measurements as in sensor implant 102b, shown in FIG. 2B. Sensor implant 102b is configured substantially the same as sensor implant 102a, with the exception of the accommodation of two sensor arrays 124 and corresponding two US transmissive windows 127. Alternatively, rather than discrete windows, the two ends of the sensor implant may be transparent and comprised of material that supports ultrasound and communication. Examples of such materials include polydimethylsiloxane (PDMS), silicone, glass and ceramic. In a further alternative, the entire housing 120 may comprise a US transparent material that also permits transmission of communications signals from the antenna structure of communication module 122.

FIG. 2C illustrates a further alternative embodiment, including multiple (N1 through Nn) sensor arrays 124, wherein sensor implant 102c is entirely a flexible construction including housing 120 being made of flexible material that also permits US signal transmission and communication signal transmission from communication module 122. An example of such a housing material includes certain polymers and ceramic. Flexible functional layers 114, 116 and 118 may be fabricated using carbon nanotubes or ultrathin silicon integrated circuit technologies. FIG. 2C also illustrates a further alternative fixation feature 128, in the form of micro hooks. Such hooks may be comprised of resilient materials such as nitinol wire or biocompatible fabrics formed as hooks of hook and loop fasteners material.

Embodiments of sensor implants disclosed herein are physically arranged in a manner to promote accurate readings regardless of migration or changes in orientation after implantation. This will include a combination of unique sensor fabrication that physically orients transducers in a fashion that will maintain focus on vessel of interest regardless of modest migration or movement of sensor away from vessel of interest. Aspects of this physical arrangement include the elongated configuration of housing 126 with plural spaced-apart sensor arrays 124 positioned on one side of the sensor implant, with appropriately positioned fixation features 128. These aspects of the disclosed sensors present a unique advantage over prior systems by making PWV calculations and blood pressure calculations based on the PWV calculations possible using only a single, unitary sensor implant to provide not only all necessary timing and dimensional data at two spaced-apart locations, but also, in some embodiments, additional patient position and movement data to allow more accurate assessment of patient hemodynamic state, and blood pressure in particular.

FIG. 3 presents a representative block diagram of major functional blocks within embodiments of implant sensors 102 as disclosed herein. As shown therein, power module 121 provides a power source in the form of a power supply comprising battery 131 and power management sub-module 132. Note that the battery can be generalized to any suitable implantable primary cell or rechargeable power source as may be devised by persons of ordinary skill. Power management sub-module 132 is configured for battery optimization to power US wireless communication, etc., with no required patient interaction to power the device, which is a substantial improvement over prior devices. Long-term monitoring can be achieved through the application of algorithms that reduce power consumption during idle times and optimize overall battery consumption, including detecting power requirements and automatedly switching appropriate modules or sub-modules to "power off" mode when power is not required in those modules or sub-modules.

Communications module 122 comprises a transceiver sub-module configured for the selected communications mode and corresponding antenna, which is preferably positioned opposite the sensor modules at or through housing 120. In some embodiments, the antenna may comprise fixation features 128 (e.g., FIGS. 2A-C). Control and signal processing module 123 may comprise memory 133, digital control 134, transmit and receive electronics sub-module 135, data converter 137 and processing sub-module 136 including at least one microprocessor. These components may be configured by persons skilled in the art based on the teachings contained herein. As will be appreciated, sensor integration with ASIC provides efficiency gains in power and size by integrating the MEMS sensor into the ASIC design. While in some embodiments pulse wave velocity and patient blood pressure may be calculated within sensor implant 102, it may be preferable to configure processing module 123 with instructions to produce a data stream from which pulse wave velocity for the blood vessel and patient blood pressure (optionally also heart rate) can be calculated.

Status sensor module 130 may comprise one or a collection of several different sensor types, including but not limited to inertial measurement unit (IMU), accelerometer, temperature sensor, electrodes for ECG or impedance, and oxygen saturation. Status sensor module 130 thus provides for monitoring of a number of different physiologic parameters, such as temperature, body position, activity, ECG and fluid retention, to compliment blood pressure measurements to assist in assessment of patient's overall condition. In most embodiments, at least a status sensor module with an accelerometer will be included to allow the data stream produced by control and processing module 123 to include information needed to adjust the blood pressure calculation to compensate for patient position and/or movement.

FIG. 3A illustrates sensor array state configurations. When multiple sensor arrays are employed, for example as in sensor implant 102c, shown in FIG. 2C, with each additional sensor array, its operation state during use (Tx or Rx) is flexible. As an example, a configuration where Sensor N1 and Sensor N2 are present is shown in FIG. 3A, wherein each sensor array has options of receive, transmit and active switching between receive and transmit. Sensor state is programmable via electronics sub-module 135.

A two-dimensional representation of a cMUT or pMUT array is shown in FIG. 3B. In this example, sensor module 124 comprises substrate 138 with an array of sensor elements 139. Ideally, the array parameters, Ds (sensor element diameter), Hs (array height) and Ls (array length), are optimized for performance within a specific sensor implant and system. For example, Ds is preferably selected based at least in part on a desired frequency of operation, thus defining a minimum vessel diameter change that can be detected by the sensor implant. Hs and Ls define number of sensor elements and are selected at least in part to optimize signal-to-noise ratio (SNR) as the pulse echo amplitude is defined by these parameters. Sensor array size can also be selected in combination with the number of plural sensor modules (as in, for example, sensor implant 102c (FIG. 2C) in order to facilitate position identification and compensation as discussed below. In some embodiments a preferred material for sensor array 138/139 is aluminium nitride (AlN), which provides US power-efficient and biocompatible sensor array substrate compatible with human implantation. Previous lead-based ultrasound transducers require 100× more energy to power sensor and are also not biocompatible for implantable use in living beings. Further details of MUT sensor constructs suitable for use in sensor implants according to the present disclosure can be found, for example, in U.S. Pat. No. 10,864,553, granted Dec. 15, 2020, entitled "Piezoelectric transducers and methods of making and using the same," and U.S. Pat. No. 10,820,888, granted Nov. 3, 2020, entitled "Miniature ultrasonic imaging system," each of which is incorporated by reference herein in its entirety.

A variety of alternative embodiments of sensor package form-factor and delivery systems will now be described in more detail with reference to FIGS. 4 through 10B. In one alternative embodiment, shown in FIG. 4, sensor implant 102d comprises housing 120 containing a sensor package as described in various embodiments above. Sensor implant 102d includes tissue-engaging tines as fixation features 128 for securing the implant in proximity to blood vessel (BV) within which measurements are to be made. Tissue-engaging tines as fixation features 128 may be configured to engage and anchor in tissues such as muscle tissue, skin tissue, outer layers of the blood vessel itself or other suitable tissues in sufficient proximity to the vessel in which measurements are to be made. The tines may have barbs or other retention features (not shown) to increase the anchoring function.

Figure 5:
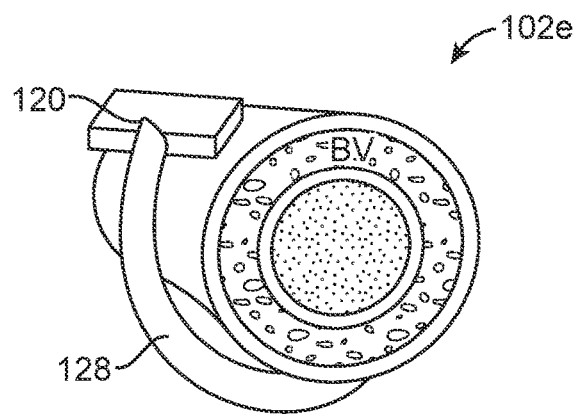
FIG. 5 is a schematic depiction of a second embodiment of a sensor according to the present disclosure.
Figure 8:
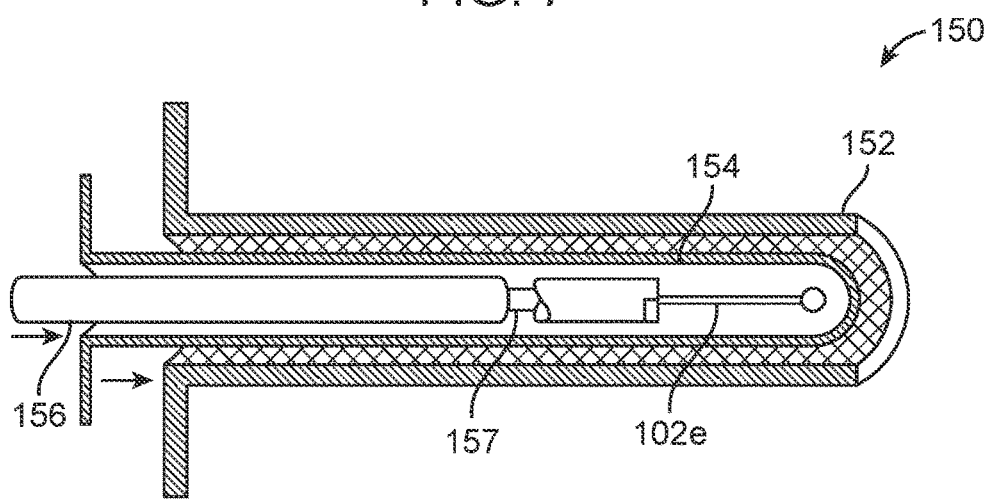
FIG. 8 is a schematic cross-section of a delivery device for a second sensor embodiment as disclosed herein.
Figure 8A:
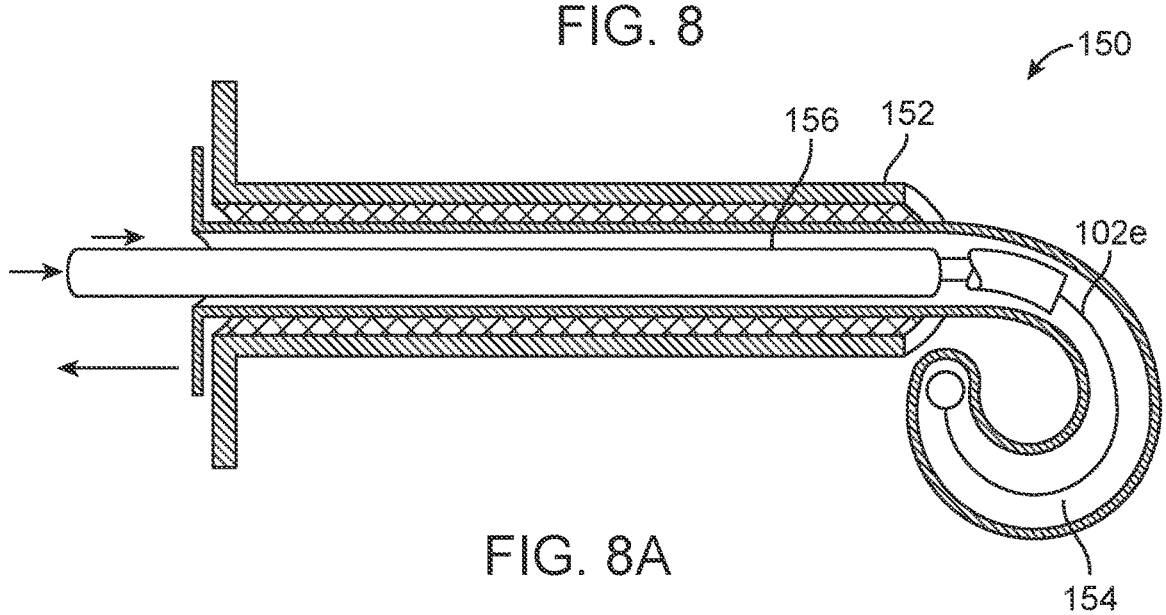
FIG. 8A is a schematic cross-section of the delivery device of FIG. 8 in a partially deployed state.

In another alternative embodiment, shown in FIG. 5, injectable sensor 102e may utilize a passive anchor system as fixation feature 128. In this example, resilient cuff as fixation feature 128 engages around the blood vessel (BV) and thus positions sensor housing 120 in close proximity to the blood vessel (BV) or in contact therewith. A method and deployment device for a resilient cuff-type fixation feature is shown in FIGS. 8-8C and described in more detail below.

Figure 6:
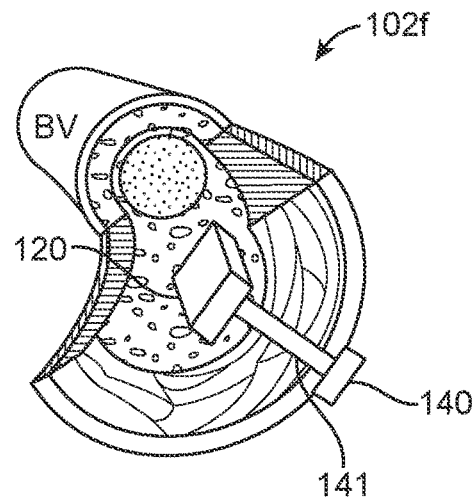
FIG. 6 is a schematic depiction of a third embodiment of a sensor according to the present disclosure.

In yet another alternative embodiment, shown in FIG. 6, sensor implant 102f comprises housing 120 with fixation feature 128 comprised of anchor element 140 disposed on the end of flexible member 141 extending from the sensor housing. In this arrangement, housing 120 of sensor implant 102f may be disposed on the inside of the blood vessel (BV) with flexible member 141 extending through the blood vessel wall, capped with anchor element 140. This arrangement may also allow the use of alternative sensor types requiring contact with the fluid to be measured, such as MEMS capacitive sensors. Sensor implant 102f may be placed with instrumentation and procedures as used for vascular electrode placement or for certain vascular closure devices having anchor member placed within the vascular lumen.

Figure 4:
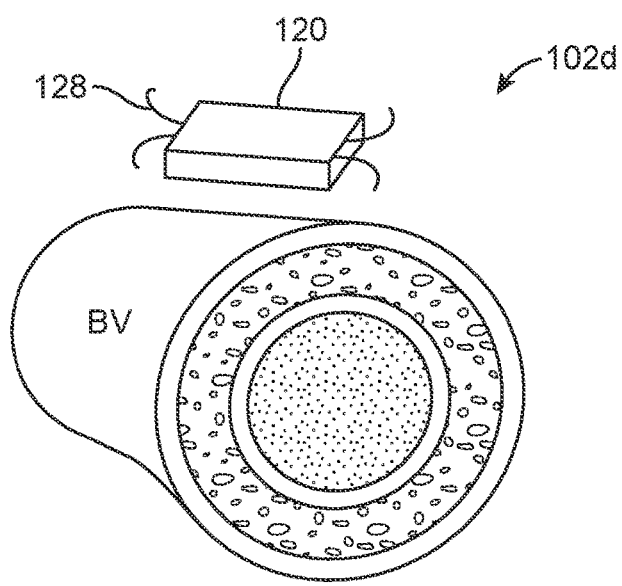
FIG. 4 is a schematic depiction of a first embodiment of a sensor according to the present disclosure.
Figure 7:
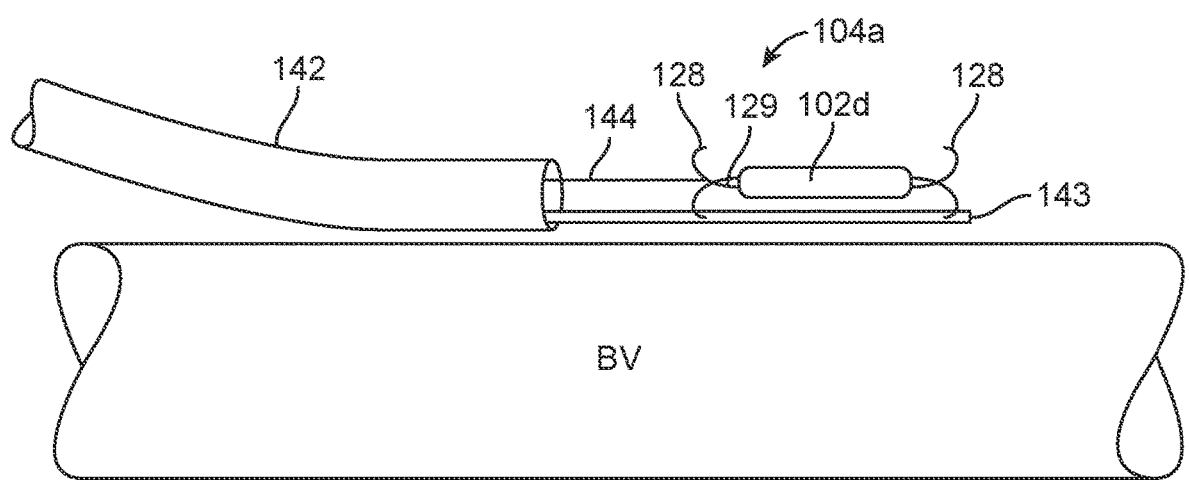
FIG. 7 is a schematic depiction of deployment of a first sensor embodiment as disclosed herein.

FIG. 7 shows deployment may be accomplished with alternative injection device 104a, including an outer sheath 142 with a sharpened, needle-like distal end terminating in a shovel-like protective extension 143. Injection device 104a otherwise may in general be configured similar to a larger-sized syringe device, wherein only the distal end portion is shown in FIG. 7. Outer sheath 142 is inserted through tissue such that protective shovel portion 143 is disposed at the intended deployment site. Tether 144 serves as both a pusher and retrieval member for deployment of sensor 102d including anchoring tines as shown in FIG. 4. When the distal end of injection device 104a is properly positioned, tether 144 is used to move sensor 102d to an exposed position over shovel-like extension 143. This allows the tines forming fixation feature 128 of sensor 102d to engage overlying tissue while protecting the blood vessel disposed below shovel-like projection 143. Tether 144 may then be disengaged and with the tines of sensor 102d engaged on overlying tissue, injection device 104a may be withdrawn. Alternatively, if positioning is not as desired, tether 144 may be used to draw sensor 102d back within sheath 142 for repositioning. Tether 144 may engage with attachment and release feature 129 as previously described. Outer sheath 142, shown in FIG. 7 with a slight distal bend, may alternatively be straight.

Figure 8B:
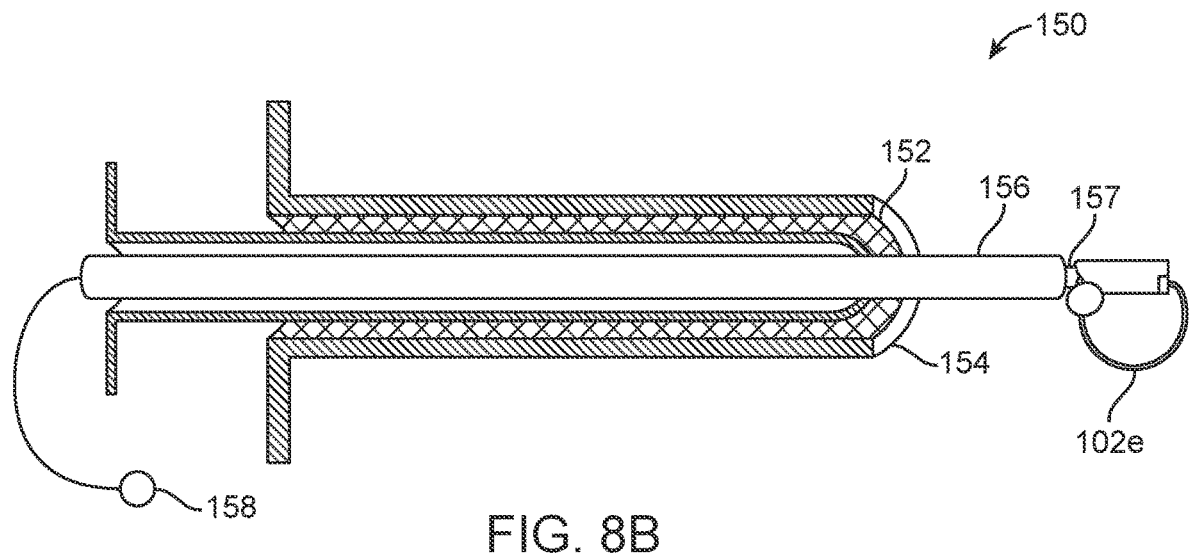
FIG. 8B is a schematic cross-section of the delivery device of FIG. 8 in a further partially deployed state.
Figure 8C:
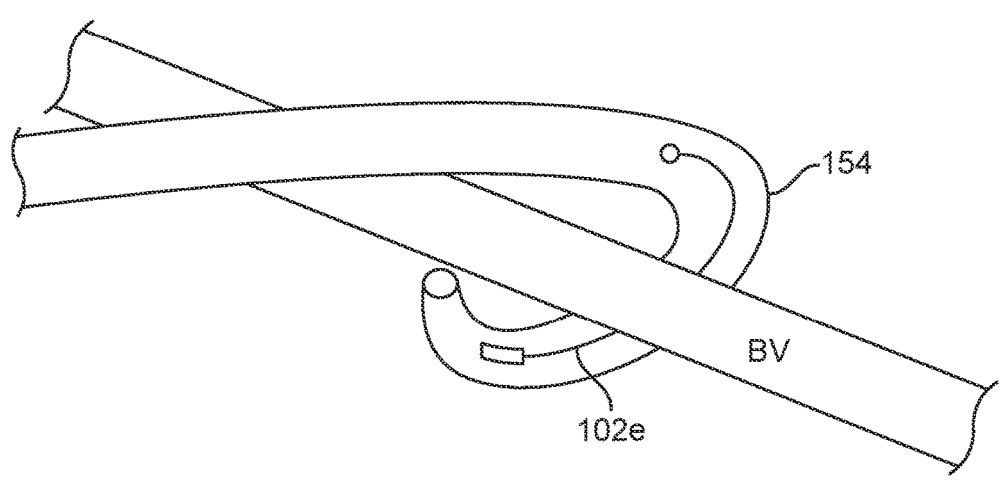
FIG. 8C is a schematic perspective view of the delivery device of FIG. 8 in a partially deployed state.

FIGS. 8, 8A-C and 9 illustrate an embodiment of injection device 150, configured for delivering an injectable sensor such as sensor 102e (FIG. 5) utilizing a resilient cuff as a passive fixation feature 128. Injection device 150 is configured generally as a syringe-type device with an outer introducer 152 surrounding an inner sheath 154 having a resiliently curved distal tip. Device injector 156 (e.g. a pusher) is concentrically disposed in the center lumen of inner sheath 154 and comprises a release and retrieval mechanism with a hook at the distal end 157 that opens and closes to release or grab sensor 102e as needed. In one embodiment the release mechanism may comprise pull wire 158 (FIG. 8B).

Figure 9:
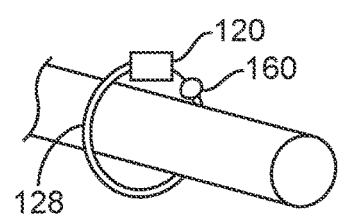
FIG. 9 is schematic depiction of an embodiment of an implant sensor after deployment as in FIGS. 8 through 8C.

After the distal end of introducer 152 is positioned subcutaneously in the area of deployment, inner sheath 154 is extended and its resilient curvature causes it to wrap around the BV at the site of interest as shown in FIGS. 8C and 9. Device injector 156 is used to position or maintain sensor 102e at the distal end of inner sheath 154 as it surrounds the blood vessel. Once positioned as shown in FIG. 8C, inner sheath 154 may be withdrawn to expose sensor 102e as in FIG. 9. Resilient anchor cuff 128 then surrounds the blood vessel (BV) while still secured to device injector 156 by retrieval mechanism hook 157. Optionally, position may be confirmed by visualization such as by ultrasound or fluoroscopy. With sensor 102e and cuff 128 positioned around the blood vessel at the site of interest, hook 157 may be disengaged by pulling release wire 158. In some embodiments, atraumatic passive ball 160 may be disposed on the end of cuff 128 opposite sensor housing 120. Anchor cuff 128 may be made of resilient, shape-memory materials such as nitinol.

Figure 10:
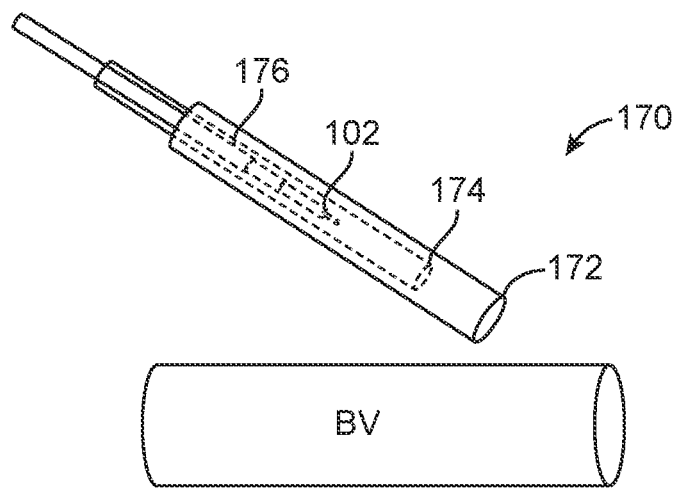
FIG. 10 is a schematic cross-section of the delivery device for the first sensor embodiment as disclosed herein.
Figure 10A:
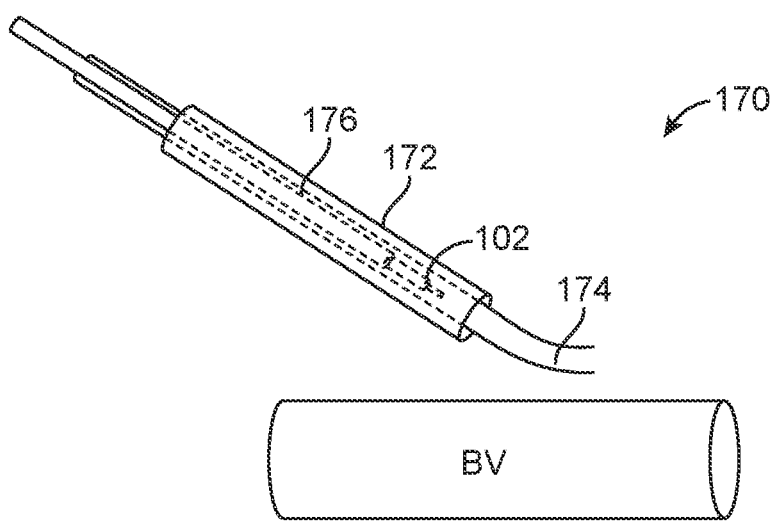
FIG. 10A is a schematic cross-section of the delivery device for the first sensor embodiment as in FIG. 10 in a partially deployed state.
Figure 10B:
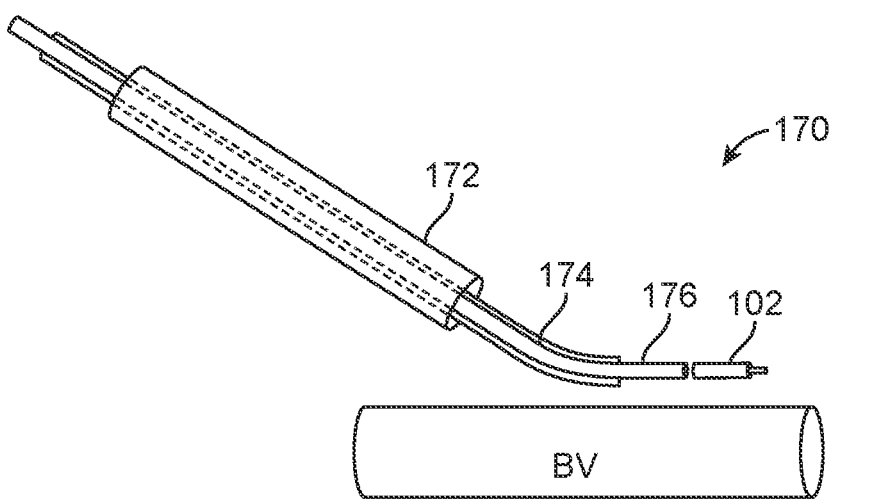
FIG. 10B is a schematic cross-section of the delivery device for the first sensor embodiment as in FIG. 10 in a further partially deployed state.

FIGS. 10, 10A and 10B illustrate a further alternative injection device 170 suitable for placement of a number of different sensor implants 102 at monitoring locations in tissue adjacent to targeted blood vessels according to the present disclosure. As shown therein, injection device 170 comprises outer introducer 172 with a sharpened, needle or syringe-like distal end, an inner atraumatic curved sheath 174 and device injector 176 sliding within inner sheath 174. Injection device 170 is also generally configured as a syringe-type device. In order to deploy sensor implant 102 with injection device 170, introducer 172 is positioned subcutaneously at the desired location, preferably under visualization, such as with ultrasound. When appropriate positioning is confirmed, inner sheath 174 is advanced out of the distal end of introducer 172. Atraumatic distal end of inner sheath 174 facilitates positioning in close proximity to a blood vessel of interest while minimizing possibility of trauma to the blood vessel during the sensor injection procedure. Distal end of inner sheath 174 may have a pre-set curve as shown in FIGS. 10A and 10B such that after exiting outer introducer the inner sheath automatically assumes the pre-set curvature thereby facilitating placement with reduced risk of trauma to the adjacent blood vessel. After inner sheath 174 is properly positioned, sensor 102 is advanced out of the distal end by device injector 176. The distal end of device injector 176 may be provided with a retrieval mechanism such as a hook as described herein. After position of sensor 102 and engagement of the fixation feature is confirmed, inner sheath 174 may be withdrawn and then the sensor disengaged from device injector 176. Injection device 170 as a whole is then withdrawn.

Figure 11:
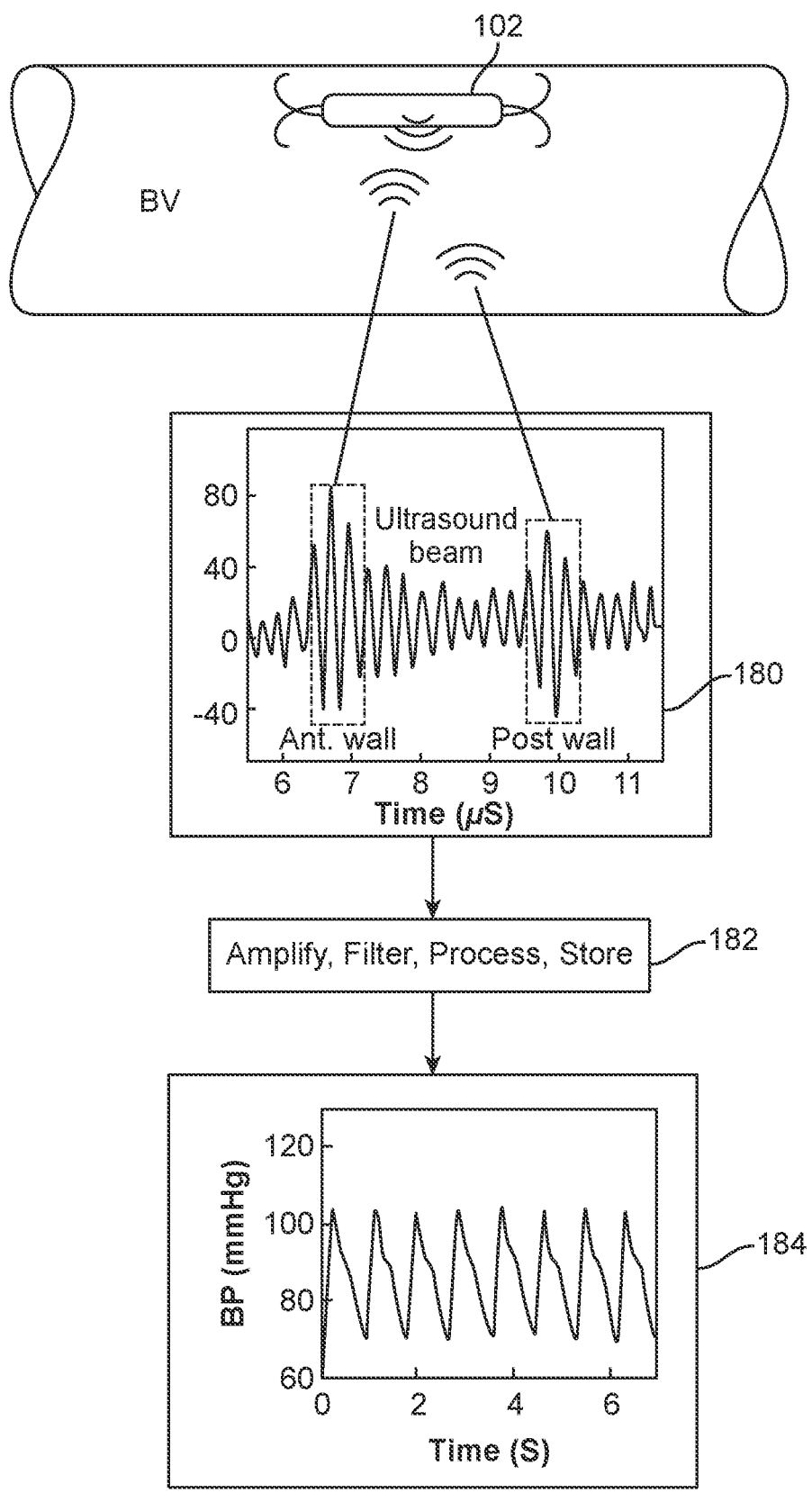
FIG. 11 is a combined schematic and block diagram illustrating sensing and signal processing according to embodiments of the present disclosure.

FIG. 11 illustrates the use of MEMS ultrasound in sensor implant 102 to determine blood pressure and other vitals based on pulse transit time and pulse wave velocity measurements 180, which are amplified, filtered and processed 182 to provide a data stream from which blood pressure over time 184 may be calculated according to known correlations between blood pressure and pulse wave velocity. Ultrasound is the transmission of sound waves through a medium. When the ultrasound sound waves reach a surface or differing medium, the wave reflects and travels back in the originating direction. The time it takes for the ultrasound wave to travel can be used to calculate the distance from the reflecting surface. This ultrasound concept may be used in embodiments of the present disclosure to calculate the diameter of the vessel wall and can be used to estimate volumetric changes in the vessel as a pulse wave travels through the vessel. Based on the wave transmission and properties, the ability to differentiate the variability in reflecting mediums, such as hard plaque or wall stiffness, is also possible.

One example of known algorithms for blood pressure calculation on this basis is described by Ma, et al., *Relation between blood pressure and pulse wave velocity for human arteries*, Proc. Natl. Acad. Sci. USA, 2018 Oct. 30; 115(44): 11144-11149 (doi: 10.1073/pnas.1814392115), Epub 2018 Oct. 15 (incorporated by reference herein in its entirety). In in vitro experiments, Ma, et al. have validated correlation of pulse wave velocity (PWV) to blood pressure through the integral of the inner artery radius to the outer artery radius after artery deformation (before and after the pulse travels through the artery). Embodiments disclosed herein employ and improve upon the concepts suggested by Ma et al. in an implanted MEMS sensor that is injected near the target vessel.

Figure 12:
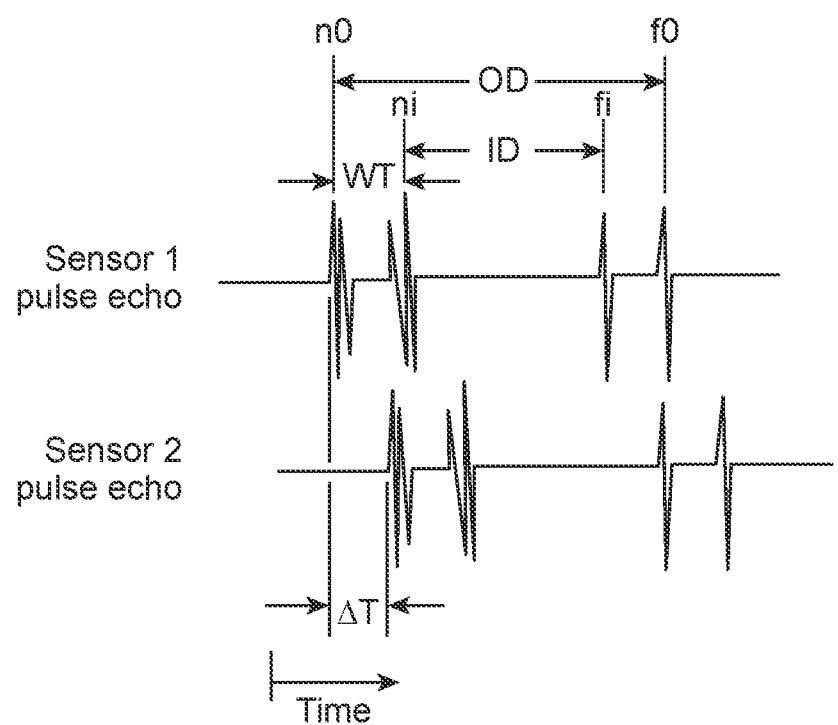
FIG. 12 is an illustration of a sample of the pulse echoes produced by a dual array sensor implant configured in accordance with the present disclosure.

Using at least two sensor arrays, for example as in sensor implant 102b, shown in FIG. 2B, vessel dimensions as well as PWV can be determined as illustrated in FIG. 12. With appropriate signal processing and focusing of the US beams, four separate US pulses can be defined, representing the outer surface of the near (proximal) wall, the inner surface of the near (proximal) wall, the inner surface of the far (distal) wall, and the outer surface of the far (distal) wall. This allows determination of not only the diameter of the inner vessel, but also the thickness of the arterial wall. Heart rate is also directly determinable from this signal over time. Table 1 sets forth the parameters identified in FIG. 12.

TABLE 1

FIG. 12 parameters

| Dimensions | | Peaks | |
|---|---|---|---|
| OD | outside diameter | no | near wall, outside |
| ID | inside diameter | ni | near wall, inside |
| WT | wall thickness | fi | far wall, inside |
| ΔT | time of travel of BP pulse from sensor 1 to sensor 1 as identified by wall movement | fo | far wall, outside |

Using these US measurements, plus the known distance between sensor 1 and sensor 2, the PWV can be calculated as PWV=(d)/ΔT. It is to be noted that the pulse echo shown can be the statistical sum of pulse echo received from several sensors and reflects all pre-processing completed in hardware.

Figure 13:
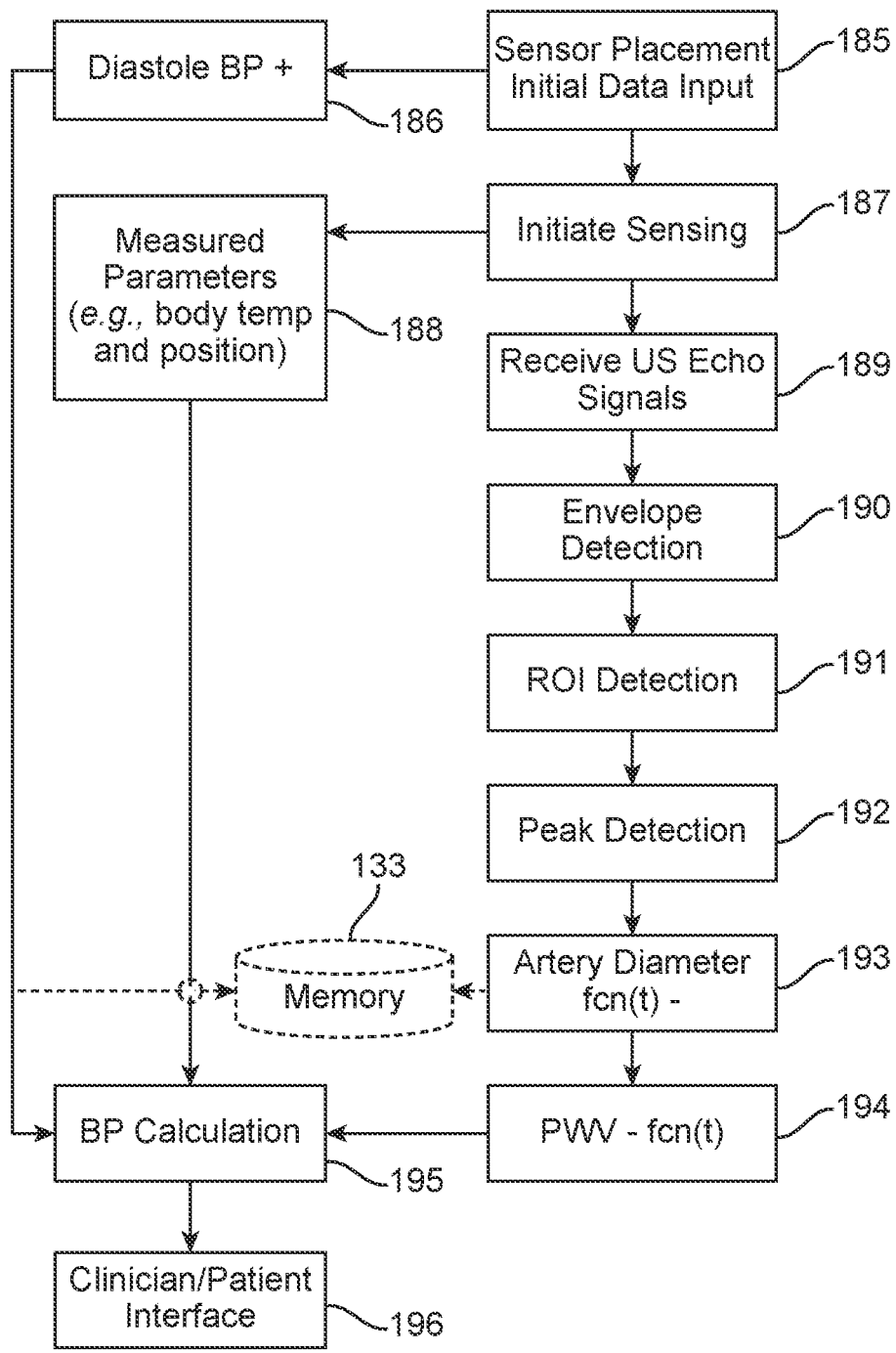
FIG. 13 is a flow diagram illustrating a signal processing methodology according to an embodiment of the present disclosure.

FIG. 13 depicts an embodiment of a process flow for determination of patient blood pressure and general hemodynamic state. Placement of sensor implants 102 according to the present disclosure as described above may be performed as an in- or outpatient procedure, employing clinically accepted practices for subcutaneous insertion. Typical placement sites include the upper arm targeting the brachial artery for monitoring, or the thoracic region targeting the subclavian artery in the delta pectoral groove for monitoring. At time of placement (step 185), patient diastolic blood pressure is measured and input to the system, for example via interface 110 (step 186). Other patient data may be input at this time to improve accuracy of hemodynamic state assessment. Such other information may include patient age, sex, weight, height and any known comorbidities. After sensor implant placement is verified, the system is initialized (step 187). At this stage, monitoring begins with US sensor modules 124 and status sensor module 130 (step 188). At a minimum, body position or changes in body position are detected (step 188) with an accelerometer included in status sensor module 130 to permit adjustment of the calculated blood pressure to take into account variations based on body position and movement. Sensor module operation may be programmed on an intermittent basis at specific periods or may be continuous or near-continuous.

US pulse echo signals, as shown in FIG. 12, are received (step 189) initially by electronics sub-module 135 for processing in control and signal processing module 123. In some embodiments, processing at this point may be minimal, such as filtering and signal amplification, with the signal data thereafter transmitted via communications module for further signal processing in external module 106 or in other networked processing environments such as network-based systems 108 or a computing system associated with user interface 110. Alternatively, in more preferred embodiments, further signal processing as described in the following steps 190-194 is executed within control and signal processing module 123 of sensor implant 102 according to instructions stored in memory sub-module 133. Regardless of locus of execution, envelope detection (step 190), region-of-interest (ROI) detection (step 191), and peak detection (step 192) are executed in accordance with known signal-processing algorithms for processing of US signals. A variety of such algorithms are well-known in the art and may be selected by persons of ordinary skill based on the teaching contained herein. With signal data appropriately processed for interpretation by the designated computing device (internal, external or networked), vessel diameter as a function of time is determined based on analysis of the US signals (step 193). Measured and recorded data stored in memory module 133 may include, for example, vessel inner and outer diameters at each US sensor array, ΔT between the different US sensor array readings, heart rate/interval, temperature and patient or sensor implant orientation.

Pulse wave velocity (PWV) is determined and recorded at step 194 based on parameters determined in prior steps. Based on determined PWV and at least the previously measured and entered Diastole BP (step 186), blood pressure is calculated (step 195), according to correlations known in the art, for example, using algorithms described by Ma et al. as explained above. Additional inputs to blood pressure calculation (step 195), which may increase accuracy of the calculated blood pressure, may include other measured parameters (step 188) such as patient activity or orientation (as determined by accelerometer or IMU in status sensor module 130) and body temperature (as determined by temperature sensor in module 130). Other parameters as described hereinabove also may be factored in by persons of ordinary skill based on the teachings of the present disclosure. Patient blood pressure and other hemodynamic parameters as measured and determined, along with measured parameters (step 188) are delivered to the clinician/patient interface, such as interface 110 (step 196). In one embodiment, calculation of blood pressure is executed in network-based systems through appropriate network connections with local control module 106.

Figure 14:
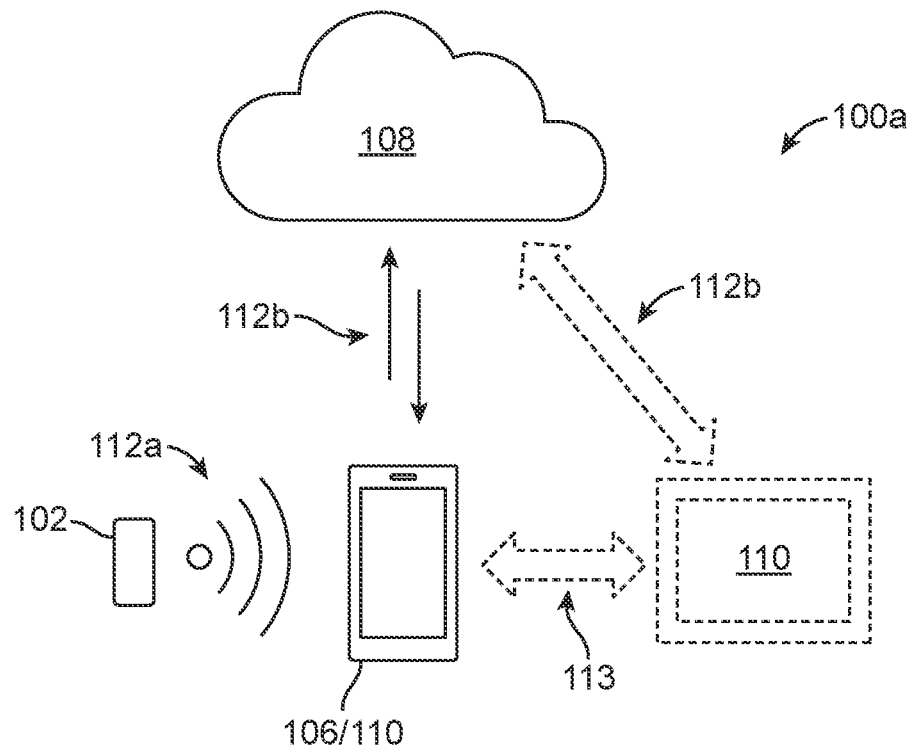
FIG. 14 is a schematic depiction of another system according to an alternative embodiment of the present disclosure

FIG. 14 illustrates a further alternative embodiment of a system 100a according to the present disclosure. In this example, sensor implant 102 includes at least two ultrasound sensor modules comprised of micromachined ultrasonic transducer arrays, a status sensor module comprised of at least an accelerometer, and a control module including at least one microprocessor and at least one memory containing instructions and configured to allow the sensor implant to perform at least sensing and processing steps 188 through 193. In this specific example, communication module 122 uses Bluetooth communication to transmit a processed data stream containing blood vessel dimension, timing and accelerometer information as needed to permit calculation of pulse wave velocity and patient blood pressure. In this example, a personal mobile device is configured as one or both of local module 106 and patient interface 110 using a mobile device app and transmits the processed data stream to a networked computer for calculation of pulse wave velocity and patient blood pressure according to stored algorithms discussed herein. Patient blood pressure information is conveyed back to the patient via the mobile device 106/110. Optionally, a separate clinician interface may receive the patient data directly from networked computing device 108 via the network or through the patient mobile device 106/110.

Parameters utilized in processing may include those parameters that are determined during initial implantation of implant sensor 102 and as may be updated as needed with periodic calibration. In some embodiments periodic calibration may include analysis to determine placement relative to initial placement location. Given the unique implant structure employing, in some embodiments (e.g. sensor implants 102b and 102c), multiple sensor MUT modules positioned at known fixed distances with respect to one another, analysis of returned US signals allows for continually accurate PWV calculation by using changes in the US-viewed orientation relative to the observed vascular structure to determine a skew factor for correcting PWV calculations. For example, using anatomical markers as detected by sensor modules 124 and interpreted by control and signal processing module 123, the system may determine that the longitudinal axis of the sensor implant, originally preferably implanted in alignment with direction of blood flow or at a known orientation with respect thereto, has become skewed relative to flow direction by a determined skew angle. The system may then recalculate the distance between N and N+1 sensor modules 124 as (cos[skew angle])/[fixed sensor module spacing]= [skew adjusted sensor spacing].

As will be appreciated by persons skilled in the art, devices, systems and methods disclosed herein, given the large and varied amount of physiological and specifically hemodynamic data generated, allow for accurate detection and classification of arrythmias, such as bradycardia, ventricular tachy-cardia, atrial fibrillation, atrial tachycardia, and sinus pause using data generated in accordance with the teaching of the present disclosure in known diagnostic algorithms. Further, one or more of the following vital signals: systolic BP, diastolic BP, mean arterial BP, Pulse Wave Velocity (PWV), blood flow, arterial stiffness, elasticity modulus, ECG waveform, heart rate, heart rhythm, atrial fibrillation, bradycardia, tachycardia, sinus pause, activity, body position, blood pressure variability, heart rate variability, endothelial function, coronary artery disease, blood oxygen saturation (O2 sat), composite score or indication of cardiovascular health and risk may be calculated, stored and uploaded to network-based systems for accurate patient assessments over extended times without requiring in-patient or clinic visits for data collection. In a further aspect of the present disclosure, patient-centered engagement apps employing user interfaces on mobile devices or home computing devices to encourage adherence and patient behaviors may be driven based on collected data and analysis thereof.

Figure 15:
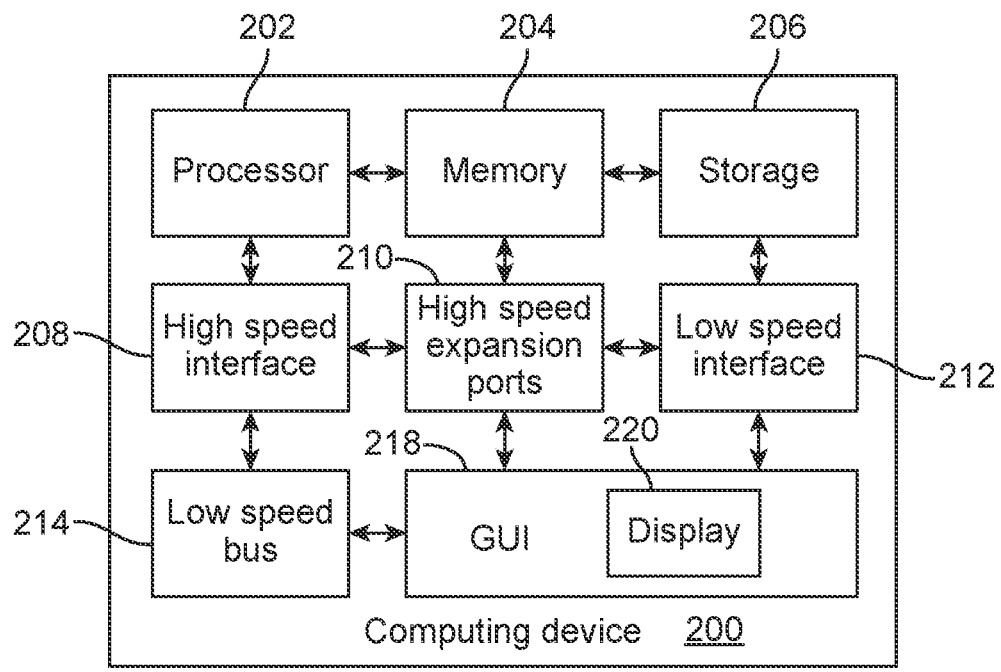
FIG. 15 is a block diagram illustrating components of computing devices which may be used to execute various aspects of the present disclosure.

In some embodiments, various aspects of the present disclosure, including, for example, local module 106, network-based modules 108, clinician user interface/application 110, and control and signal processing module 123 among others, may be executed as one or more computing devices 200 as illustrated in FIG. 15. In this example, computing device 200 includes one or more processors 202, memory 204, storage device 206, high-speed interface 208 connecting to memory 204 and high-speed expansion ports 210, and a low speed interface 212 connecting to low speed bus 214 and storage device 206. Each of the components 202, 204, 206, 208, 210, and 212, are interconnected using various busses or other suitable connections as indicated in FIG. 15 by arrows connecting components. Processor 202 can process instructions for execution within the computing device 200, including instructions stored in the memory 204 or on the storage device 206 to display graphical information via GUI 218 with display 220, or on an external user interface device, coupled to high speed interface 208. In other implementations, multiple processors and/or multiple busses may be used, as appropriate, along with multiple memories and types of memory. Also, multiple computing devices 200 may be connected, with each device providing portions of the necessary operations (e.g., as a server bank, a group of blade servers, or a multi-processor system).

Memory 204 stores information within the computing device 200. In one implementation, the memory 204 is a computer-readable medium. In one implementation, the memory 204 is a volatile memory unit or units. In another implementation, the memory 204 is a non-volatile memory unit or units. Memory within implant 102 may store, for example data from ultrasound readings representing vessel dimensions and sensor timing and patient movement based on accelerometer data. Such data also may comprise a data stream communicated from the sensor implant computing device and may be stored in a network-based memory along with pulse wave velocity and blood pressure calculations executed in a network-based computing device.

Storage device 206 is capable of providing mass storage for the computing device 200, and may contain information such as the database of tile display information described hereinabove. In one implementation, storage device 206 is a computer-readable medium. In various different implementations, storage device 206 may be a floppy disk device, a hard disk device, an optical disk device, or a tape device, a flash memory or other similar solid state memory device, or an array of devices, including devices in a storage area network or other configurations. In one implementation, a computer program product is tangibly embodied in an information carrier. The computer program product contains instructions that, when executed, perform one or more methods, such as those described above. The information carrier is a computer- or machine-readable medium, such as the memory 204, the storage device 206, or memory on processor 202.

High speed controller 208 manages bandwidth-intensive operations for the computing device 200, while low speed controller 212 manages lower bandwidth-intensive operations. Such allocation of duties is exemplary only. In one implementation, high-speed controller 208 is coupled to memory 204, display 220 (e.g., through a graphics processor or accelerator), and to high-speed expansion ports 210, which may accept various expansion cards (not shown). In the implementation, low-speed controller 212 is coupled to storage device 206 and low-speed expansion port 214. The low-speed expansion port, which may include various communication ports (e.g., USB, Bluetooth, Ethernet, wireless Ethernet) may be coupled to one or more input/output devices as part of GUI 218 or as a further external user interface, such as a keyboard, a pointing device, a scanner, or a networking device such as a switch or router, e.g., through a network adapter.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" "computer-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the systems and techniques described here can be implemented on a computer having a display device (e.g., an LED, OLED or LCD display) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of wired or wireless digital data communication (e.g., a communication network). Examples of communication networks include a local area network ("LAN"), a wide area network ("WAN"), and the Internet.

The computing system can include clients and servers. A client and server are generally remote from each other and typically interact through a communication network. The relationship of client and server arises by virtue of computer programs running on the respective computers and having a client-server relationship to each other.

Other features and advantages include that the implanted sensor system is actively powered with a rechargeable battery that is integrated into the implanted sensor system, which has the benefit of minimizing patient burden while allowing long-term (for months to years) of functional use. The implanted sensor system will automatically connect to the external charging and communication module when the patient is within range of the charging and communication module. When connected the external charging and communication system will charge the battery in the implanted sensor system. A benefit of the active implanted sensor system with automatic charging is that the patient does not need to take action to recharge the battery. The implanted sensor system has a longevity of months to years.

Implanted/injectable sensor systems as disclosed herein may also store sensor signal data (for instance, up to a week) in the memory chip that is designed into the ASIC and memory module of the implanted sensor system. This can further reduce the burden to the patient to be in range of the external charging and communication system and reduces the risk of lost data.

Disclosed delivery embodiments also provide an ability to retract and reposition the implanted/injectable sensor prior to final fixation to find optimal sensor placement. This is due to the functions of the injection tool in combination with the fixation design of the implanted sensor system. One benefit of this feature is to enable sensor repositioning for optimal sensor accuracy.

Implanted/injectable sensor systems as disclosed may employ an RF communication module to enable transfer of implanted sensor signal data to the external charging and communication system. The RF communication module optionally may be designed to support charging of the implanted sensor system.

Implanted/injectable sensors as disclosed are hermetically sealed to protect the sensor components for longer term implantation to address chronic conditions. The sensor package may be coated with a biocompatible material that prevents tissue growth and blood clotting.

Summary of aspects of embodiments of the present disclosure:
1. An active implantable sensor system for measuring and recording cardiovascular signals from a blood vessel comprising an injectable sensor module configured for delivery by injection through a syringe-like delivery device into tissue adjacent a blood vessel.
2. An active implantable sensor system for measuring and recording cardiovascular signals from a blood vessel, including systolic and diastolic blood pressure, and comprised of:
    a. a sensing module that utilizes MEMS piezoelectric sensors (ultrasound) and may also incorporate other sensors such as a MEMS strain gauge sensor, and piezoelectric sensors;
    b. an ASIC and memory module that processes incoming signals and stores data for up to a week;
    c. power and communication module that incorporates a battery and antenna for communication and optional charging; and
    d. fixation design, architecture and approach that minimizes trauma and allows for explant or repositioning.
3. Cardiovascular monitor is fixated outside the target blood vessel, with:
    a. a novel fixation mechanism that allows the device to be repositioned, explanted, and prevents disruption or occlusion of the vessel being monitored;
    b. primary cell battery or rechargeable battery with at least 6 months longevity;
    c. wirelessly transmits data to an external source/network-based system; and
    d. improved bio-coating on the exterior of cardiovascular monitor that minimizes encapsulation.
4. Sensing Module that:
    a. collects sensor data every 10-30 minutes for programmed duration (24 hours, 48 hours, 1 week, 1 month . . . );
    b. includes MEMS diaphragm pressure sensor that measures blood pressure and correlates to sphygmomanometer blood pressure;
    c. monitors and detects blood pressure, activity, body position; and
    d. calibrates and recalibrates pressure measurements post-maturation phase.
5. Algorithm Module, with novel algorithms, that is:
    a. physician-programmable for detection and monitoring zones, duration and frequency of measurements, and ability for patient to access recording.
6. External Patient Module that allows:
    a. recharging of cardiovascular monitor; and
    b. wireless transmission of raw data to cloud and Algorithm Module.
7. Web-based software solution that enables physician programming of algorithm module, and ability to review patient cardiovascular data.

The foregoing has been a detailed description of illustrative embodiments of the disclosure. It is noted that in the present specification and claims appended hereto, conjunctive language such as is used in the phrases "at least one of X, Y and Z" and "one or more of X, Y, and Z," unless specifically stated or indicated otherwise, shall be taken to mean that each item in the conjunctive list can be present in any number exclusive of every other item in the list or in any number in combination with any or all other item(s) in the conjunctive list, each of which may also be present in any number. Applying this general rule, the conjunctive phrases in the foregoing examples in which the conjunctive list consists of X, Y, and Z shall each encompass: one or more of X; one or more of Y; one or more of Z; one or more of X and one or more of Y; one or more of Y and one or more of Z; one or more of X and one or more of Z; and one or more of X, one or more of Y and one or more of Z.

Various modifications and additions can be made without departing from the spirit and scope of this disclosure. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present disclosure. Additionally, although particular methods herein may be illustrated and/or described as being performed in a specific order, the ordering is highly variable within ordinary skill to achieve aspects of the present disclosure. Accordingly, this description is meant to be taken only by way of example, and not to otherwise limit the scope of this disclosure or of the inventions as set forth in following claims.

It is claimed:
1. A hemodynamic monitoring method, comprising:
subcutaneously placing a sensor implant in a patient in tissue adjacent a target blood vessel;
generating a data stream with said sensor implant from which pulse wave velocity of the target blood vessel during a sensing period can be determined; and
transmitting said data stream to a computing device configured to determine pulse wave velocity for the target blood vessel and blood pressure for the patient using said data stream;

wherein said generating a data stream comprises:
  generating and receiving pulse echoes representing inner and outer walls of the target blood vessel at first and second sensing locations with first and second ultrasound sensors;
  detecting changes in target blood vessel diameter at the first and second sensing locations based on said pulse echoes; and
  measuring a time between detecting of a change in target blood vessel diameter at the first sensing location and at the second sensing location.

2. The method of claim 1, further comprising:
  transmitting an initial patient diastolic blood pressure to the computing device;
  determining, with the computing device, the pulse wave velocity of the target blood vessel during the sensing period based on the transmitted data stream;
  determining, with the computing device, the patient blood pressure during the sensing period using the initial patient diastolic blood pressure, determined pulse wave velocity and inner and outer wall diameters for the target blood vessel; and
  transmitting at least the patient blood pressure to a user interface accessible by at least one of the patient or a patient care provider.

3. The method of claim 1, wherein said subcutaneously placing comprises:
  injecting the sensor implant into the patient tissue using an injection device having a hollow sheath with a sharpened distal end; and
  positioning the sensor implant in tissue at a placement location within about 2 mm to about 50 mm of the target blood vessel.

4. A hemodynamic monitoring method, comprising:
  subcutaneously placing a sensor implant in a patient in tissue adjacent a target blood vessel;
  generating a data stream with said sensor implant from which pulse wave velocity of the target blood vessel during a sensing period can be determined; and
  transmitting said data stream to a computing device configured to determine pulse wave velocity for the target blood vessel and blood pressure for the patient using said data stream;
  wherein said generating a data stream with the sensor implant comprises:
    generating data representative of a change in target blood vessel diameter at a first location;
    generating data representative of a change in target blood vessel diameter at a second location;
    generating data representative of a distance between the first location and the second location; and
    generating data representative of a time difference between the change in target blood vessel diameter at the first location and the second location.

5. The method of claim 4, wherein said generating the data representative of the changes in target blood vessel diameter at the first and second locations comprises ultrasound imaging of the target blood vessel with first and second ultrasound transducers disposed in the sensor implant.

6. The method of claim 4, wherein said generating a data stream with said sensor implant further comprises generating data representative of target blood vessel inner and outer diameter.

7. The method of claim 4, wherein said generating a data stream with said sensor implant further comprises generating data representative of patient movement or change in position.

8. The method of claim 7, wherein said generating data representative of patient movement or change in position comprises detecting patient movement with an accelerometer disposed in the sensor implant.

9. A hemodynamic monitoring method, comprising:
  subcutaneously placing a sensor implant in a patient in tissue adjacent a target blood vessel;
  generating a data stream with said sensor implant from which pulse wave velocity of the target blood vessel during a sensing period can be determined; and
  transmitting said data stream to a computing device configured to determine pulse wave velocity for the target blood vessel and blood pressure for the patient using said data stream;
  wherein said sensor implant is a unitary sensor implant comprising first and second spaced apart ultrasound transducers, an accelerometer and a temperature sensor; and
  wherein the first and second sensor ultrasound transducers each comprise an ultrasonic transducer array, and said generating a data stream comprises:
    generating and receiving pulse echoes representing inner and outer walls of the target blood vessel at a first sensing location with the first ultrasound transducer;
    generating and receiving pulse echoes representing inner and outer walls of the target blood vessel at a second sensing location with the second ultrasound transducer;
    detecting changes in target blood vessel diameter at the first and second sensing locations based on said pulse echoes;
    measuring a time between detecting of a change in target blood vessel diameter between the first and second sensing locations;
  detecting patient movement or changes in patient position with the accelerometer; and
  detecting patient temperature with the temperature sensor.

10. The method of claim 9, further comprising placing plural of said unitary sensor implants and generating unique said data streams with each said unitary sensor implant.

11. The method of claim 2, wherein the computing device is a networked computing device.

12. The method of claim 2, wherein the computing device comprises a personal mobile device.

13. A hemodynamic monitoring method, comprising:
  subcutaneously placing a sensor implant in a patient in tissue adjacent a target blood vessel;
  generating a data stream with said sensor implant from which pulse wave velocity of the target blood vessel during a sensing period can be determined; and
  transmitting said data stream to a computing device configured to determine pulse wave velocity for the target blood vessel and blood pressure for the patient using said data stream;
  wherein said subcutaneously placed sensor implant includes first and second ultrasound sensors spaced apart at fixed distance, and said generating and transmitting steps comprise:
    receiving an ultrasound imaging signal from the first ultrasound sensor depicting imaging of a target blood vessel at a first sensing location;

detecting a cardiac cycle pulse in the first imaging signal;
receiving an ultrasound imaging signal from the second ultrasound sensor depicting imaging of the target blood vessel at a second sensing location spaced at a sensing distance from the first sensing location;
detecting the cardiac cycle pulse in the second imaging signal;
determining the sensing distance based on the fixed distance and the first and second imaging signals;
measuring time between the detection of the cardiac cycle pulse at the first and second sensing locations;
detecting patient movement during a timeframe encompassing the detecting of the cardiac cycle pulse at the first and second sensing locations; and
transmitting a signal containing data representing the detected patient movement, determined sensing distance and measured time for receipt at a computing device outside a patient's body configured to determine patient blood pressure during the timeframe based on said data contained in the transmitted signal.

14. The method of claim 13, wherein said receiving, detecting, determining and measuring steps are performed within the sensor implant and said transmitting step is initiated by the sensor implant.

15. The method of claim 13, further comprising determining target blood vessel inner and outer diameters based on the first and second imaging signals.

16. The method of claim 13, further comprising:
receiving the transmitted signal at a local communications module in proximity to the patient;
transmitting the data contained in said signal to the computing device at a remote location;
transmitting an initial patient diastolic blood pressure to said computing device;
determining patient blood pressure in the computing device based on the transmitted data, target blood vessel inner and outer diameters, and initial patient blood pressure; and
receiving the patient blood pressure determination at the local communications module.

17. The method of claim 13, further comprising subcutaneously placing a sensor implant in a patient tissue adjacent the target blood vessel by injecting the sensor implant into the patient tissue using an injection device having a hollow sheath with a sharpened distal end.

18. A hemodynamic monitoring method, comprising:
subcutaneously placing a sensor implant in a patient in tissue adjacent a target blood vessel;
generating a data stream with said sensor implant from which pulse wave velocity of the target blood vessel during a sensing period can be determined; and
transmitting said data stream to a computing device configured to determine pulse wave velocity for the target blood vessel and blood pressure for the patient using said data stream;
wherein:
said subcutaneously placing the sensor implant in a patient in tissue comprises placing the sensor implant at a placement location outside a target blood vessel within about 2 mm to about 50 mm of the target blood vessel, said implant comprising at least one sensor configured to detect changes in vessel diameter at first and second spaced apart sensing locations along said vessel, wherein a distance between said first and second sensing locations along said vessel varies based on orientation of the implant with respect to the vessel;
said generating a data stream with said sensor implant comprises
detecting vessel diameter at the first and second sensing locations; and
generating a data stream correlated to a sensing period, the data stream comprising
data representative of a change in target vessel diameter at the first sensing location,
data representative of a change in target vessel diameter at the second sensing location,
data representative of the distance between the first and second sensing locations,
data representative of a time difference between the change in target blood vessel diameter at the first sensing location and the second sensing location,
data representative of patient movement or change in position, and
data representative of vessel inner and outer diameter; and
said transmitting said data stream comprises transmitting the data stream to an external system, whereby said data stream is accessible by a computing device to determine pulse wave velocity for the vessel and patient blood pressure during the sensing period based on said data stream.

19. The method of claim 18, further comprising automatically adjusting the data representative of the distance between the first and second sensing locations to compensate for changes in orientation of the sensor implant with respect to the target blood vessel.

20. The method of claim 19, wherein:
said sensor implant comprises first and second ultrasound imaging sensors spaced apart at a fixed sensor spacing; and
said automatically adjusting the data representative of the distance between the first and second sensing locations comprises determining a skew factor based on changes in implant orientation relative to anatomical structure detected by said ultrasound imaging sensors.

21. The method of claim 18, further comprising:
initializing the sensor implant after placement through a healthcare provider device; and
receiving patient blood pressure determination from the computing device.

22. The method of claim 21, wherein:
said initializing includes transmitting patient diastolic blood pressure
to the external system accessible by the computing device; and
said receiving patient blood pressure comprises receiving an initial blood pressure determination at the healthcare provider device and receiving subsequent blood pressure determinations at a patient device.

23. The method of claim 22, further comprising separately receiving the subsequent blood pressure determinations at the healthcare provider device.

* * * * *